(12) United States Patent
Gupta

(10) Patent No.: US 11,857,654 B2
(45) Date of Patent: Jan. 2, 2024

(54) NHAP CONTAINING ORAL COMPOSITION

(71) Applicant: Sonia Gupta, Kihei, HI (US)

(72) Inventor: Sonia Gupta, Kihei, HI (US)

( * ) Notice: Subject to any disclaimer, the term of this patent is extended or adjusted under 35 U.S.C. 154(b) by 0 days.

(21) Appl. No.: 17/497,301

(22) Filed: Oct. 8, 2021

(65) Prior Publication Data

US 2023/0114022 A1   Apr. 13, 2023

(51) Int. Cl.
A61K 8/24 (2006.01)
A61K 8/92 (2006.01)
A61K 8/19 (2006.01)
A61Q 11/00 (2006.01)

(52) U.S. Cl.
CPC .................. A61K 8/24 (2013.01); A61K 8/19 (2013.01); A61K 8/922 (2013.01); A61Q 11/00 (2013.01); A61K 2800/413 (2013.01); A61K 2800/87 (2013.01); A61K 2800/92 (2013.01)

(58) Field of Classification Search
CPC . A61K 8/19; A61K 8/24; A61K 8/922; A61K 2800/413; A61K 2800/87; A61K 2800/92; A61Q 11/00
See application file for complete search history.

(56) References Cited

U.S. PATENT DOCUMENTS

| | | | |
|---|---|---|---|
| 1,045,633 A | 11/1912 | Arthur et al. | |
| 3,935,306 A | 1/1976 | Roberts et al. | |
| 4,374,822 A | 2/1983 | Ralph et al. | |
| 5,302,375 A | 4/1994 | David | |
| 5,496,541 A | 3/1996 | Cutler | |
| 5,670,138 A | 9/1997 | Venema et al. | |
| 5,833,959 A | 11/1998 | Atsumi et al. | |
| 6,177,097 B1 | 1/2001 | Hanke | |
| 6,221,341 B1 | 4/2001 | Montgomery | |
| 8,434,933 B2 | 5/2013 | Brito et al. | |
| 9,161,895 B1 | 10/2015 | Baig et al. | |
| 9,180,318 B2 | 11/2015 | Deng et al. | |
| 10,179,096 B2 | 1/2019 | Singh et al. | |
| 2003/0198606 A1 | 10/2003 | Kim et al. | |
| 2004/0101493 A1* | 5/2004 | Scott | A61K 8/8117 424/49 |
| 2005/0019276 A1 | 1/2005 | Nathoo et al. | |
| 2009/0263497 A1 | 10/2009 | Brito et al. | |
| 2010/0034871 A1* | 2/2010 | Mikkelsen | A61K 8/02 424/440 |
| 2015/0004560 A1* | 1/2015 | Arnold | A61Q 11/00 424/53 |
| 2015/0238399 A1 | 8/2015 | Spaid et al. | |
| 2021/0069096 A1 | 3/2021 | Debaun | |

* cited by examiner

Primary Examiner — Adam C Milligan
Assistant Examiner — Amanda Michelle Petritsch

(57) ABSTRACT

Embodiments relate to a composition comprising nanohydroxyapatite (NHAP) in an amount about 0.5 wt. % to about 50 wt. % of the composition having a particle size in a range of about 20-100 nm, an abrasive, a sweetener, and a natural oil, wherein the composition does not contain glycerin and fluoride, wherein the composition is alkaline and a dental product, and wherein the natural oil is a plant product.

8 Claims, 14 Drawing Sheets
(14 of 14 Drawing Sheet(s) Filed in Color)

A

B

A

B

C

A

B

C

D

E

NHAP CONTAINING ORAL COMPOSITION

FIELD OF THE INVENTION

The present disclosure is related to an alkaline dental composition containing nanohydroxyapatite. The composition is free of glycerin, fluoride, and a surfactant.

BACKGROUND OF INVENTION

U.S. Pat. No. 9,161,895B1 states that oral care products such as toothpastes and mouthwashes are routinely used by consumers as part of their oral care hygiene regimens. Oral care products are formulated to provide both therapeutic and cosmetic hygiene benefits. Therapeutic benefits include caries prevention which is typically delivered through the use of various fluoride salts; gingivitis prevention by the use of antimicrobial agents such as triclosan, cetylpyridinium chloride, stannous fluoride, zinc citrate or essential oils; and hypersensitivity control through the use of ingredients such as strontium chloride, stannous fluoride, or potassium nitrate. Cosmetic benefits include control of plaque and calculus formation, removal and prevention of tooth stains, tooth whitening, breath freshening, and overall improvements in mouth oral confidence from a health as well as aesthetic standpoint.

Another benefit that is increasingly important for complete oral health is providing protection and resistance to dental erosion due to the permanent effects of harsh abrasives and acids on teeth.

The incidence and severity of dental erosion is on the rise with the increase in the consumption of acidic beverages and juices. The pH and titratable acidity of acidic beverages have been identified as the main causative agents in the initiation and progression of dental erosion.

BR112013025952B1 states that the products we enjoy as consumers, unfortunately, often have a negative impact on our teeth. Sour drinks and sweets, for example, can result in tooth erosion, attacking the enamel that lines and protects the teeth. Also, tobacco products and beverages such as coffee and tea can stain teeth over time and result in a less attractive smile. In addition to what we consume, the natural balance between the hydroxyapatite of the tooth being dissolved from the tooth enamel and the hydroxyapatite being formed on or in the teeth from the naturally occurring substances in the saliva is continually altered. Such alteration can produce unattractive teeth with cariogenic conditions.

Caries is another condition that is detrimental to tooth health and structural integrity. Caries is the result of the tooth caries process results in calcium phosphate mineral loss from tooth substrate induced by localized plaque microbiological acid production from fermentable dietary substrates. If left uninhibited, the caries process results in significant mineral loss from teeth, which manifests as a loss of structural integrity and the formation of a cavity.

US9161895B1 states that remineralization refers to the process of repair of acid damaged tooth structure—by the recrystallization of mineral salts on the tooth architecture. Remineralization processes are a natural protective feature of saliva against the formation of cavities, as saliva is supersaturated with calcium phosphate tooth mineral salts. Remineralization is accelerated by fluoride ions in a solution which increase local supersaturation with respect to fluoridated calcium phosphate deposition. Fluoride uptake or fluoridation refers to the application of fluoride agents through topical treatments into tooth substrates.

Much of the toothpaste sold in the United States has 1,000 to 1,100 parts per million fluorides. In European countries, such as the UK or Greece, the fluoride content is often higher; a sodium fluoride content of 0.312% w/w (1,450 ppm fluoride) or stannous fluoride content of 0.454% w/w (1,100 ppm fluoride) is common. All these concentrations are likely to prevent tooth decay, according to a 2019 Cochrane review. Concentrations below 1,000 ppm are not likely to be preventive as the preventive effect increases with concentration.

Although fluoride is a preventative to tooth decay, it can be fatal when swallowed in specific amounts. Another major concern for children under 12 months of age is dental fluorosis. Dental fluorosis happens if a child ingests excessive fluoride through toothpaste causing nausea and vomiting.

Therefore, the Food and Drug Administration (FDA) has issued a guideline, stating that each toothpaste having fluoride as an ingredient should have a warning label. The warning should carry the following quoted information "keep out of reach of children under the age of six. If more than is used for brushing is accidentally swallowed, get medical help or contact a Poison Control Center right away.

U.S. Ser. No. 10/179,096B2 states that currently available tooth-bleaching compositions have a significant disadvantage in that they cause tooth sensitization in over 50% of patients. Tooth sensitivity may result from the movement of fluid through the dentinal tubules, which is sensed by nerve endings in the tooth, due to the presence of glycerin, propylene glycol and polyethylene glycol in these compositions. This can result in varying amounts of tooth sensitivity following exposure of the teeth to heat, cold, overly sweet substances, and other causative agents.

Therefore, there is a long felt need to develop a composition that provides complete oral health along with a range of therapeutic and aesthetic benefits, including anticaries, antimicrobial, antigingivitis, antiplaque, antisensitivity, anticalculus and anti-erosion, as well as antiodor, mouth refreshment and moisturization, stain removal, stain control and tooth whitening, and is safe to be used and does not contain fluoride.

SUMMARY OF INVENTION

The invention provides complete oral health along with a range of therapeutic and aesthetic benefits, including anticaries, antimicrobial, antigingivitis, antiplaque, anti sensitivity, anticalculus and anti-erosion, as well as antiodor, mouth refreshment and moisturization, stain removal, stain control and tooth whitening, and is safe to be used and does not contain fluoride.

The invention discloses an alkaline dental composition with essential oils and does not contain fluoride.

The present invention relates to NHAP containing oral composition.

An embodiment relates to a composition comprising nanohydroxyapatite (NHAP) in an amount about 0.5 wt. % to about 70% of the composition having a particle size in a range of about 10-100 nm, an abrasive, a sweetener, and a natural oil, wherein the composition does not contain glycerin and fluoride, wherein the composition is alkaline and a dental product, and wherein the natural oil is a plant product.

In one embodiment, the abrasive comprises sodium bicarbonate.

In an embodiment, the sweetener comprises xylitol, erythritol or *Stevia*.

In one embodiment, the natural oil comprises a coconut oil.

In an embodiment, the composition comprises no surfactant.

In one embodiment, the composition further comprises a flavoring agent.

In an embodiment, the particle size is about 10-50 nm.

In an embodiment, the flavoring agent comprises peppermint oil.

In an embodiment, NHAP is in a suspension.

In an embodiment, the suspension of the NHAP is about 0.5 wt. % to about 10 wt. % of the composition.

In one embodiment, the composition comprises the natural oil in an amount from about 10 wt. % to about 90 wt. % of the composition.

An article comprising a fabric and a dental composition, wherein the dental composition comprises a suspension of nanohydroxyapatite (NHAP) in an amount about 0.1 wt. % to about 50 wt. % of the dental composition having a particle size in a range of about 10-50 nm, an abrasive, a sweetener, and a natural oil, wherein the composition does not contain glycerin and fluoride, wherein the composition is alkaline, and wherein the natural oil is a plant product.

In an embodiment, the article comprises a floss or a wipe.

In an embodiment, the fabric comprises a natural product comprising a seaweed, cotton, a bamboo charcoal, corn, hemp, or silk.

In an embodiment, the dental composition comprises no surfactant.

In an embodiment, the dental composition further comprises a flavoring agent.

An embodiment relates to a method to formulate the composition of claim 1 comprising grinding the abrasive, the sweetener and the NHAP to form a mixture and combining the mixture with the natural oil.

BRIEF DESCRIPTION OF THE FIGURES

The patent or application file contains at least one drawing executed in color. Copies of this patent or patent application publication with color drawing(s) will be provided by the Office upon request and payment of the necessary fee.

Color drawings have been submitted in this application because in figures such as FIG. 2 and FIG. 3 show the change in teeth before and after use of toothpaste composition according to disclosed invention. The variation in color gives obvious visual cues about efficiency of the composition. Similarly, FIG. 13, FIG. 16 and FIG. 17 also gives cues about teeth illustrating effects of disclosed invention in the composition. Thus, the color drawing is the only practical medium by which aspects of the claimed subject matter may be accurately conveyed.

The figures are furnished with the application to understand the invention seeking patenting. It shall not be construed as the only way to perform the invention seeking patenting.

Figure 1:
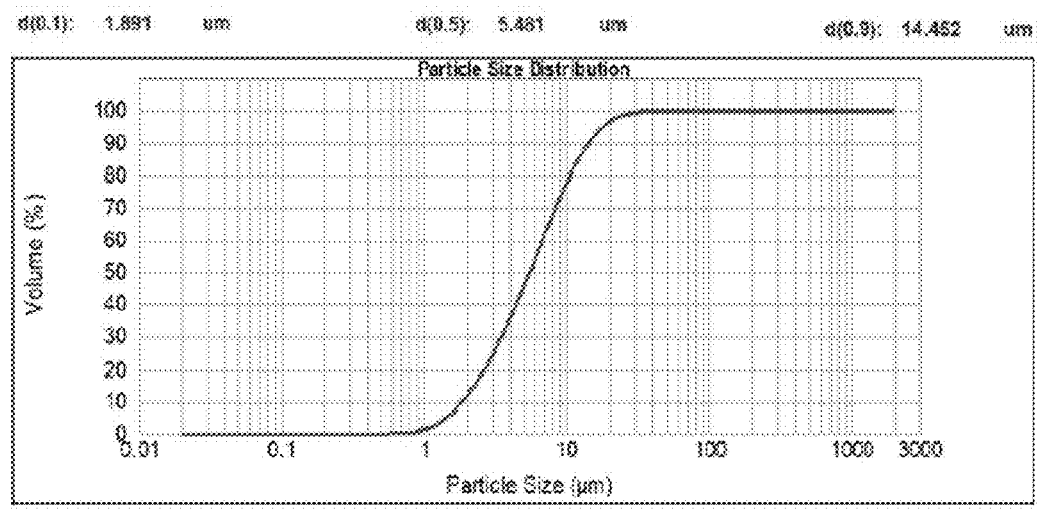

FIG. 1 shows particle size distribution of NHAP in powder.

Figure 2:
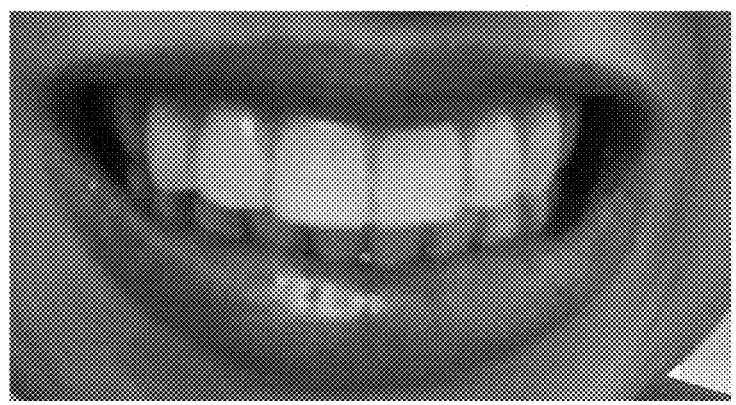

FIG. 2 shows teeth before use of toothpaste according to at least one embodiment of this invention.

Figure 3:
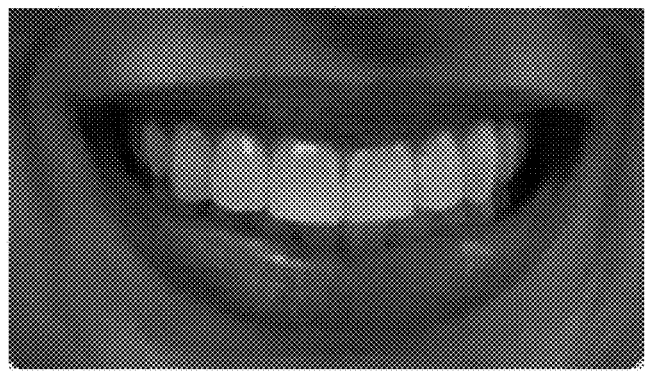

FIG. 3 shows teeth after use of toothpaste according to at least one embodiment of this invention.

Figure 4:

FIG. 4 shows a sample of citric acid (CA) and baking soda (BS) used in composition of one of the embodiments of this invention. The pH is measured using pH paper, which shows yellow and bluish color in the case of citric acid and baking soda, respectively, indicating their acidic and basic ph.

Figure 5:

FIG. 5 shows pH change in composition in mixing of baking soda and citric acid used in composition of one of the embodiments of this invention.

Figure 6:
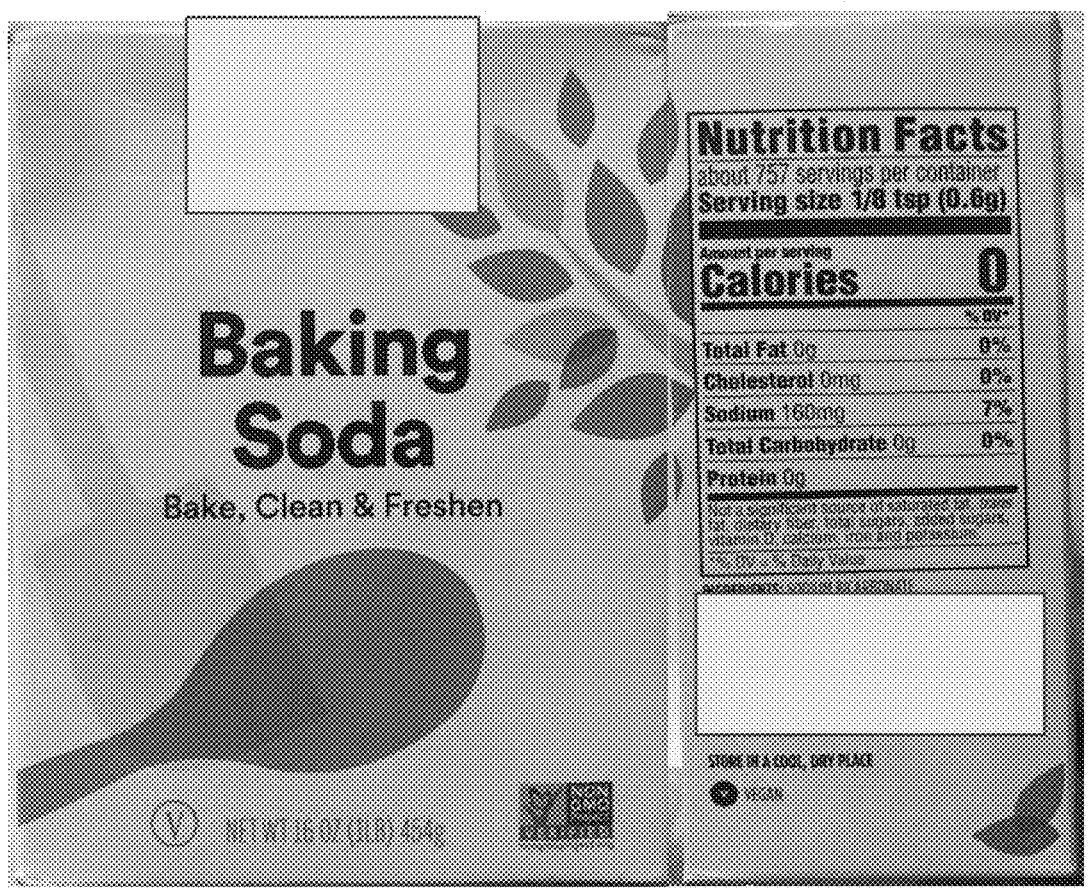

FIG. 6 shows a sample of baking soda used in composition of one of the embodiments of this invention.

Figure 7:

FIG. 7 shows a sample of xylitol used in composition of one of the embodiments of this invention.

Figure 8:

FIG. 8 shows a sample of citric acid used in composition of one of the embodiments of this invention.

Figure 9:
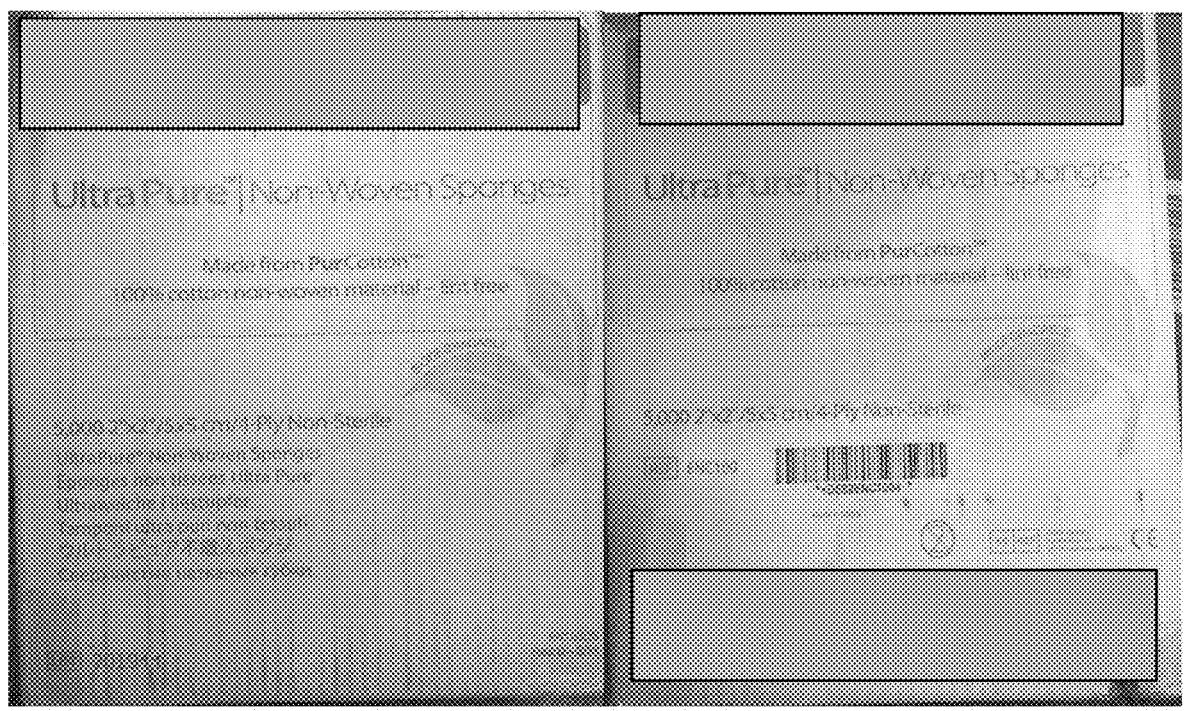

FIG. 9 shows a sample of non-woven sponges used in composition of one of the embodiments of this invention.

Figure 10:
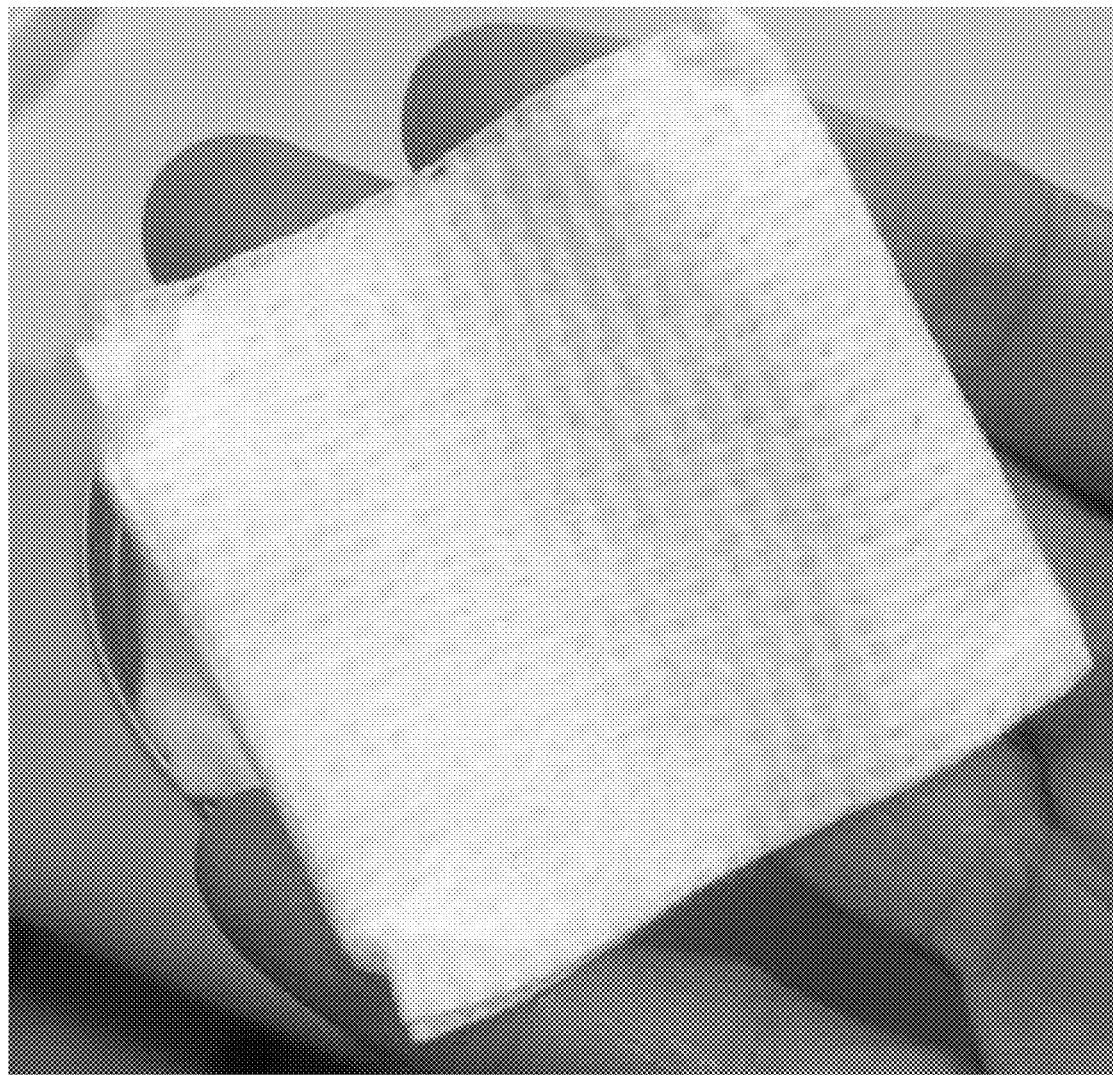

FIG. 10 shows a wipe used as a dental product according to embodiments of this invention.

Figure 11:

FIG. 11 shows a sample of wipes according to one of the embodiments of the invention.

Figure 12:
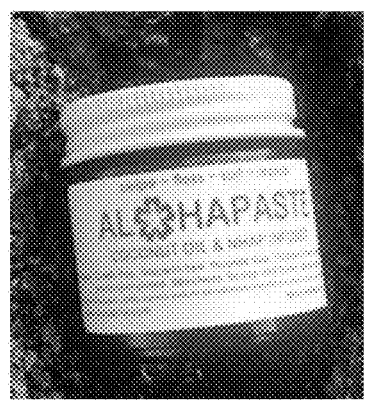

FIG. 12 shows a sample paste according to one of the embodiments of the invention.

Figure 13:
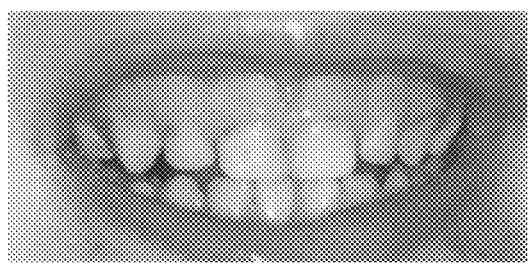
Figure 13:
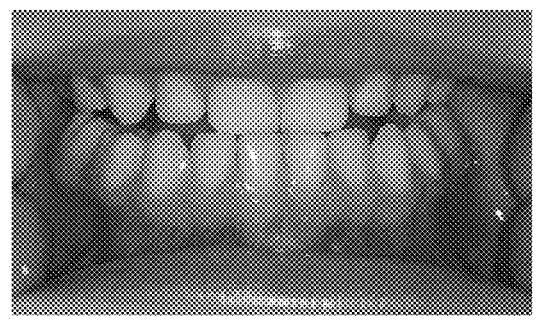
Figure 13:

FIG. 13 shows comparison of primary teeth of a child before and after use of toothpaste according to at least one embodiment of this invention. (A) teeth before applying toothpaste (B & C) cleaned teeth after using toothpaste.

Figure 14:
Figure 14:
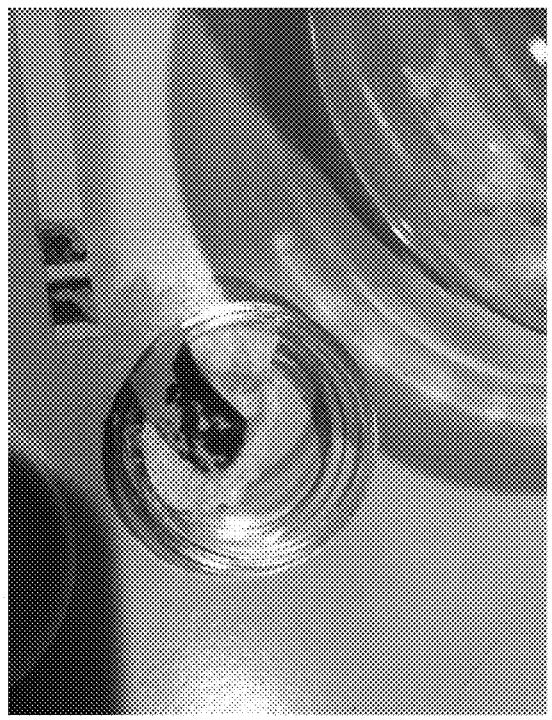

FIG. 14 (A-B) shows pH of the composition according to one of the embodiments of the invention.

Figure 15:
Figure 15:
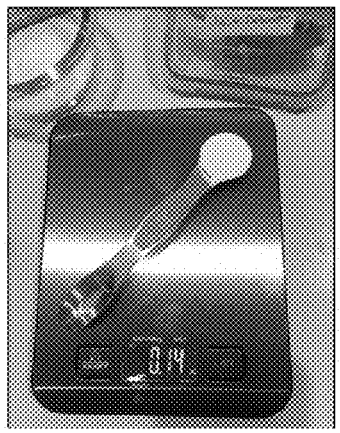
Figure 15:
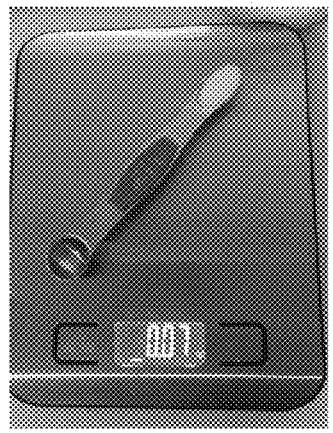
Figure 15:
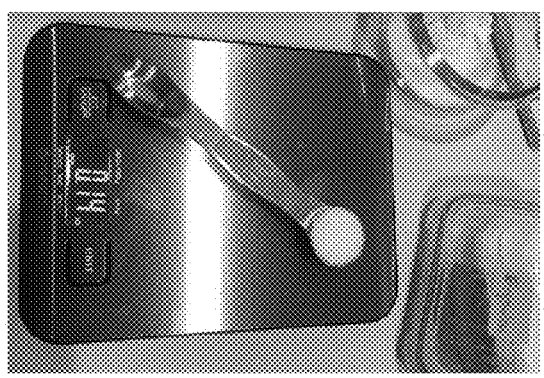
Figure 15:
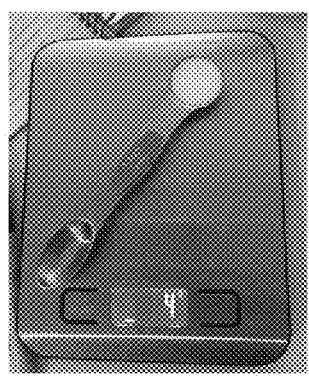

FIG. 15 (A-E) shows weight measurement of ingredients according to one of the embodiments of the invention.

Figure 16:
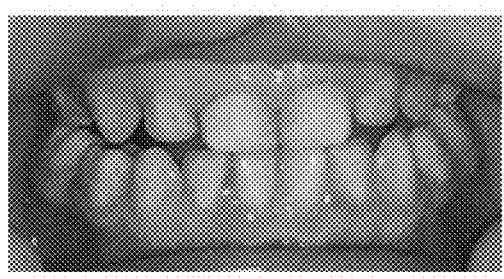
Figure 16:
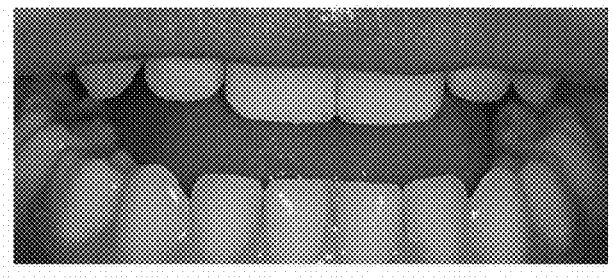

FIG. 16 shows comparison of primary teeth of a child before and after use of wipes according to at least one embodiment of this invention: (A) teeth before applying wipes (B). cleaned teeth with wipes according to this invention.

Figure 17:
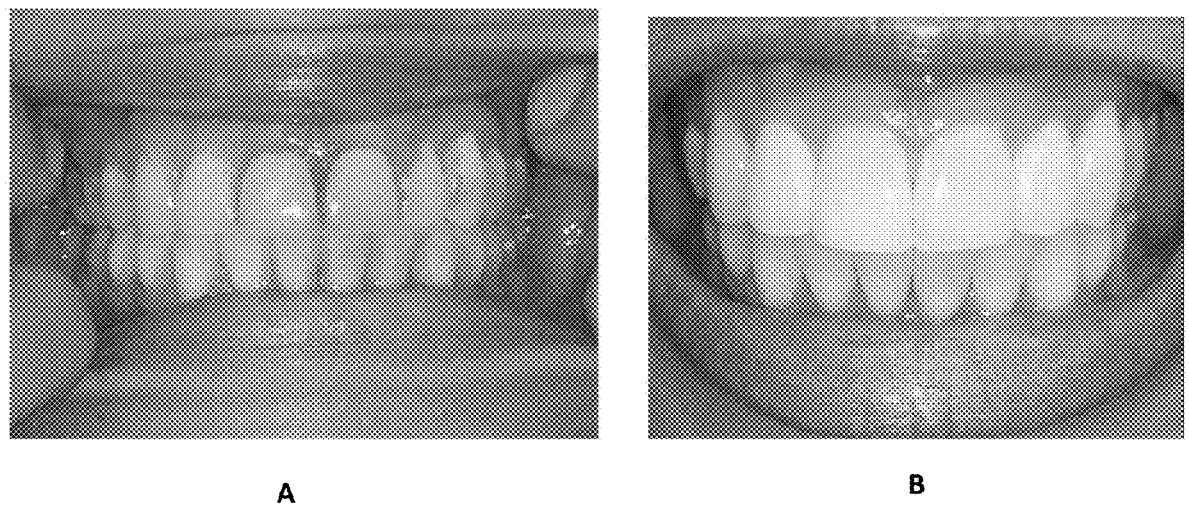

FIG. 17 shows comparison of adult teeth before and after use of toothpaste according to at least one embodiment of this invention (A) teeth before applying toothpaste (B). cleaned teeth after applying toothpaste according to this invention.

DETAILED DESCRIPTION

Definitions and General Techniques

For simplicity and clarity of illustration, the figures illustrate the general manner of construction. Descriptions and details of well-known features and techniques may be omitted to avoid unnecessarily obscuring the present disclosure. Additionally, elements in the drawing are not necessarily drawn to scale. For example, the dimensions of some of the elements in the figures may be exaggerated relative to other elements to help improve understanding of embodiments of the present disclosure. The same reference numerals in different figures denotes the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements but may include other elements not expressly listed or inherent to such a process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Unless otherwise defined herein, scientific, and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

No element, act, or instruction used herein should be construed as critical or essential unless explicitly described as such.

As defined herein, two or more elements are "integral" if they are comprised of the same piece of material. As defined herein, two or more elements are "non-integral" if each is comprised of a different piece of material.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

The methods and techniques of the present invention are generally performed according to conventional methods well known in the art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

All compositions and ingredients including percentage of ingredient according to this invention is to be construed by weight basis unless state otherwise.

The following terms and phrases, unless otherwise indicated, shall be understood to have the following meanings.

One Teaspoon (tsp) equal to 4.2 gram (g or gm) or 4.9 milliliters (ml).

One Tablespoon (tbsp) equal to 14.7 gram (g or gm) or 14.78 milliliters (ml).

One drop equal to 0.05 milliliters (ml).

"Composition" herein refers to oral composition or dental composition. The term "oral composition" includes, but is not limited to, prevention and/or treatment of oral diseases, maintenance of oral health, reduction, or elimination of bad breath, whitening of teeth and prevention of gingival degradation and/or prevention of caries. It is intended to include various embodiments of compositions that are useful for all aspects of oral hygiene.

"Hydroxyapatite", also called hydroxyapitite (HA), is a naturally occurring mineral form of calcium apatite with the formula $Ca_5(PO_4)_3(OH)$, but it is usually written $Ca_{10}(PO_4)_6(OH)_2$ to denote that the crystal unit cell comprises two entities.

Hydroxyapatite is the hydroxyl end member of the complex apatite group. The $OH^-$ ion can be replaced by fluoride, chloride, or carbonate, producing fluorapatite or chlorapatite. It crystallizes in the hexagonal crystal system. Pure hydroxyapatite powder is white. Naturally occurring apatite can, however, also have brown, yellow, or green colorations, comparable to the discolorations of dental fluorosis.

Up to 50% by volume and 70% by weight of human bone is a modified form of hydroxyapatite, known as bone mineral. Carbonated calcium-deficient hydroxyapatite is the main mineral of which dental enamel and dentin are composed. Hydroxyapatite crystals are also found in the small calcifications, within the pineal gland and other structures, known as *Corpora arenacea* or 'brain sand'.

In an embodiment, remineralization of tooth enamel involves the reintroduction of mineral ions into demineralized enamel. Hydroxyapatite is the main mineral component of enamel in teeth. During demineralization, calcium and phosphorus ions are drawn out from the hydroxyapatite. The mineral ions introduced during remineralization restore the structure of the hydroxyapatite crystals.

In an embodiment, hydroxyapatite is used within dentistry and oral and maxillofacial surgery, due to its chemical similarity to hard tissue.

In an embodiment, synthetic hydroxyapatite (SHA) is proven to provide successful outcomes in alveolar socket preservation. Socket grafting using synthetic hydroxyapatite can result in successful bone regeneration.

"Nanohydroxyapatite" or nano-hydroxyapatite or nano hydroxyapatite or like "NHAP" is a form of calcium crystal. It is nano sized form of hydroxyapatite. It works by remineralizing, it replaces missing sections of minerals that have dissolved out of enamel or bone by bonding directly to the bone or tooth surfaces. It can also stimulate new bone growth by acting on the cells that cause regrowth.

Nanohydroxyapatite has properties such as high surface energy, high electrostatic field, strong polarization force, and high affinity for enamel and cementum, and it can enhance enamel surface remineralization, face microhardness, tooth whitening and reinforce the resistance to acid. Nanohydroxyapatite can also adsorb amino acids and polysaccharides like protein and glucose inhibiting the production of cariogenic speckle and managing dental caries and these two types of periodontal disease.

Nanohydroxyapatite possesses a remineralizing effect on teeth and can be used to prevent damage from carious attacks. In the event of an acid attack by cariogenic bacteria, nanohydroxyapatite particles can infiltrate pores on the tooth surface to form a protective layer. Furthermore, nanohydroxyapatite may have the capacity to reverse damage from carious assaults by either directly replacing deteriorated surface minerals or acting as a binding agent for lost ions. In the future, there are possibilities for using nanohydroxyapatite for tissue engineering and repair. The main and most advantageous feature of nanohydroxyapatite is its biocompatibility. It is chemically like naturally occurring hydroxyapatite and can mimic the structure and biological function of the structures found in the resident extracellular matrix. Therefore, it can be used as a scaffold for engineering tissues such as bone and cementum. It may be used to restore cleft lips and palates and refine existing practices such as preservation of alveolar bone after extraction for better implant placement.

NHAP in toothpaste may combat dental hypersensitivity. They aid in the repair and remineralization of the enamel, thus helping to prevent tooth sensitivity. Tooth enamel can become demineralized due to various factors, including acidic erosion and dental caries. If left untreated, this can lead to the exposure of dentin and subsequent exposure of the dental pulp. NHAP in toothpaste showed positive results in aiding the remineralization of dental enamel.

In an embodiment, NHAP is in the form of a particle.

In an embodiment, NHAP is equal or more effective than fluoride.

In an embodiment, NHAP in composition is about 0.025% w/w, 0.05% w/w, 0.1% w/w, 0.5% w/w, 1% w/w, 2% w/w, 3% w/w, 4% w/w, 5% w/w, 10% w/w, 15% w/w, 20% w/w, 25% w/w, 30% w/w, 35% w/w, 40% w/w, 45% w/w, 50% w/w or more. In an another embodiment, a range of NHAP in the composition is selected from a minimum value being either 0.025% w/w, 0.05% w/w, 0.1% w/w, 0.2% w/w, 0.3% w/w, 0.4% w/w, 0.5% w/w, 1% w/w, 5% w/w, 12% w/w, 17% w/w, 20% w/w, 22% w/w, 25% w/w, 30% w/w, 32% w/w, 35% w/w, 37% w/w, 40% w/w and a maximum value being either 10% w/w, 13% w/w, 15% w/w, 20% w/w, 25% w/w, 35% w/w, 40% w/w, 45% w/w, 50% w/w, 55% w/w, 60% w/w, 70% w/w or more.

"Particle" means a substance being a solid having a shape which can be geometrically determined. The shape can be regular or irregular. Particles can typically be analyzed with respect to e.g., grain size (e.g., mean grain or particle size) and grain or particle size distribution.

In an embodiment, particle size of NHAP can vary from 0.1 nm to 100 nm. In an embodiment, a size range of NHAP particles is selected from 0.1 nm, 1 nm, 5 nm, 10 nm, 20 nm, 30 nm, 40 nm, or 50 nm. Maximum size of nanoparticle particles is selected from 20 nm, 30 nm, 40 nm, 50 nm, 75 nm, 100 nm or more. These NHAP particles can be in the form of suspension.

In an embodiment, particle size of NHAP can vary from 0.1 nm to 100 nm. In an embodiment, a size range of NHAP particles is selected from a minimum value being either 0.1 nm, 1 nm, 5 nm, 10 nm, 20 nm, 30 nm, 40 nm, or 50 nm and a maximum value being either 20 nm, 30 nm, 40 nm, 50 nm, 75 nm, 100 nm or more. In an embodiment, a size of particle is less than 100 nm, less than 75 nm, less than 50 nm, less than 25 nm, less than 20 nm, less than 10 nm or lesser.

"Powder" is a dry, bulk solid composed of many particles that may flow freely when shaken or tilted. Powders are a special subclass of granular materials, although the terms powder and granular are sometimes used to distinguish separate classes of material. In particular, powders refer to those granular materials that have the finer grain sizes, and that therefore have a greater tendency to form clumps when flowing.

In an embodiment, particle size of NHAP powder can vary from 0.5 micron, 1 micron, 2 micron, 3 micron, 4 micron, 5 micron, 6 micron, 7 micron, 8 micron, 9 micron, 10 micron or more.

In an embodiment, a paste or gel might become a powder after it has been thoroughly dried but is not considered a powder when it is wet because it does not flow freely. Substances like dried clay, although are dry solids composed of very fine particles, are not powders unless crushed because they have too much cohesion between the grains, and therefore do not flow freely like a powder. A liquid flow differently than a powder, because a liquid cannot resist any shear stress and therefore it cannot reside at a tilted angle without flowing (that is, it has zero angle of repose.) A powder on the other hand is a solid, not a liquid, because it may support shear stresses and therefore may display an angle of repose.

In an embodiment, nanohydroxyapatite, has been shown to be biomimetic and biocompatible and more effective than fluoride at remineralizing teeth. "Biomimetic," refers to the body recognizing, and "Biocompatibility" is related to the behavior of biomaterials. Biocompatibility refers to the ability to perform as a substrate that will support the appropriate cellular activity, including the facilitation of molecular and mechanical signaling systems, to optimize tissue regeneration, without eliciting any undesirable effects in those cells, or inducing any undesirable local or systemic responses in the eventual host.

"Teeth", as used herein, refers to natural teeth as well as artificial teeth or dental prosthesis. A tooth (plural teeth) is a hard, calcified structure found in the jaws (or mouths) of many vertebrates and used to break down food. Some animals, particularly carnivores and omnivores, also use teeth to help with capturing or wounding prey, tearing food, for defensive purposes, to intimidate other animals often including their own, or to carry prey or their young. The roots of teeth are covered by gums. Teeth are not made of bone, but rather of multiple tissues of varying density and hardness that originate from the embryonic germ layer, the ectoderm.

The term, "baby teeth" or "primary teeth", also informally known as, milk teeth, or temporary teeth, are the first set of teeth in the growth and development of humans and other diphyodonts, which include most mammals but not elephants, kangaroos, or manatees which are polyphyodonty. Deciduous teeth develop during the embryonic stage of development and erupt (break through the gums and become visible in the mouth) during infancy. They are usually lost and replaced by permanent teeth, but in the absence of their permanent replacements, they can remain functional for many years into adulthood.

Dental caries, also known as tooth decay, is one of the most prevalent chronic diseases among children worldwide. This oral condition involves bacterial infection which demineralizes and destroys tooth tissues. In primary dentition, extensive tooth decay is the most common dental disease. An extensive carious lesion affects at least half of a tooth and possibly involves the pulp.

The term "permanent teeth" or "permanent dentition" is comprised of 32 teeth. There are 16 teeth in the maxilla and 16 in the mandible. In each arch there are two central incisors, two lateral incisors, two canines, four premolars, and six molars.

"Remineralization", as used herein, means the in-situ generation of hydroxyapatite in teeth. It includes layers in teeth from 10 nm to 6 microns and, preferably, from about 75 nm to 5 microns and, most preferably, from 150 nm to 4 microns.

Tooth whitening or tooth bleaching is the process of lightening the color of teeth.

"Tooth sensitivity" is a dental pain, which is sharp in character and of short duration, arising from exposed dentin surfaces in response to stimuli, typically thermal, evaporative, tactile, osmotic, chemical, or electrical; and which cannot be ascribed to any other dental disease.

Teeth sensitivity can be reduced by applying the composition of the present invention to the tooth surface according to the method of the present invention. The composition may be applied by any device or applicator, using traditional methods, as described in detail elsewhere in this specification, or typically associated with dental use. In one embodiment, a composition that reduces dental sensitivity using one or more human fingers is applied to one or more teeth.

In an embodiment, the present invention decreases tooth sensitivity by about 10%, 15%, 20%, 30%, 40%, 50%, 60%, 70%, 80%, 90% or 100% after application.

"Abrasive" is broadly defined as material, often a mineral, that is used to shape or finish a workpiece through rubbing which leads to part of the workpiece being worn away by friction. According to present invention, abrasive includes insoluble particles designed to help remove plaque from the teeth. The removal of plaque inhibits the accumulation of tartar (calculus) helping to minimize the risk of gum disease.

In an embodiment, abrasive could be, but not limited to, particles of aluminum hydroxide ($Al(OH)_3$), calcium carbonate ($CaCO_3$), sodium bicarbonate, various calcium hydrogen phosphates, various silicas and zeolites.

Abrasives which may be used in conventional amounts such as 20-80%, or more, of the formulations. Abrasives include, without limitation, particles of aluminum hydroxide (Al $(OH)_3$), alumina trihydrate and/or dehydrate; calcium pyrophosphate; magnesium trisilicate; insoluble sodium metaphosphate, bicarbonates such as sodium bicarbonate, calcium carbonate ($CaCO_3$), dibasic calcium phosphate, calcium hydrogen phosphates, silicas including dental silica thickener, zeolites, liponite, laponite, hydroxyapatite ($Ca_5(PO_4)_3OH$), fluorapatite, and mica.

In an embodiment, the amount of abrasive may vary from about 3-60 wt. % of total dental composition for example from about 3 wt. % to about 10 wt. %, from about 10 wt. % to about 20 wt. %, from about 20 wt. % to about 30 wt. %, from about 30 wt. % to about 40 wt. %, from about 40 wt. % to about 50 wt. % or from about 50 wt. % to about 60 wt. % of total dental composition.

In an another embodiment, a range of abrasive in the composition is selected from a minimum value being either about 0.5% w/w, about 1% w/w, about 5% w/w, about 12% w/w, about 17% w/w, about 20% w/w, about 22% w/w, about 25% w/w, about 30% w/w, about 32% w/w, about 35% w/w, about 37% w/w, about 40% w/w and a maximum value being either about 10% w/w, about 13% w/w, about 15% w/w, about 20% w/w, about 25% w/w, about 35% w/w, about 40% w/w, about 45% w/w, about 50% w/w, about 55% w/w, about 60% w/w, about 70% w/w or more.

"Sweetener" is a substance that can be used to sweeten another substance.

In one embodiment, sweeteners can be natural or artificial, but are not sugars in the conventional sense. So, glucose, sucrose and fructose are generally not included, or if included only included in relatively small amounts. One category of useful "natural" sweeteners are sugar alcohols including, for example, xylitol, arabitol, ribitol, mannitol, isomalt, lactitol, maltitol, sorbitol, erythritol, and monk fruit. Not only can these provide sweetness, they also often adjust and enhance viscosity. "Artificial" sweeteners may be used in place of some or all of the other sweeteners. These include saccharine, aspartame, Stevia, sucralose, and derivatives (SPLENDA). Honey may also be used.

In an embodiment, total amount of sweeteners may vary widely with the number and type used, their relative sweetness, the flavor to be used in the formulations, and the degree of taste masking that may be required. Amount of sweeteners may vary from about 0.25% wt./wt. as much as about 50% wt./wt. But generally, the total amount of sweeteners, particularly when using natural sweeteners such as sugar alcohols, ranges from between about 5 to about 40% wt./wt. In certain embodiments, the amount of sweetener may vary from about 5 to about 10% wt./wt., from about 10% to about 20% wt./wt., from about 20% to about 30% wt./wt., or from about 30% to about 40% wt./wt.

In an embodiment, the amount of sweetener is typically from 0.005% to 5% by weight of composition for example, from about 0.005% to about 0.05%, optionally from about 0.05% to about 1%, optionally from about 1% to about 2%, or optionally from about 2% to about 3%, optionally from about 3% to about 4%, optionally from about 4% to about 5%, by weight of the composition of a sweetener.

"Xylitol" is a chemical compound with the formula $C_5H_{12}O_5$, or $HO(CHOH)_3OH$; specifically, one particular stereoisomer with that structural formula. It is a colorless or white crystalline solid that is soluble in water. It can be classified as a polyalcohol and a sugar alcohol, specifically an alditol.

"Erythritol" is a chemical compound, a sugar alcohol, used as a food additive and sugar substitute. It is naturally occurring and is made from corn using enzymes and fermentation. Its formula is $C_4H_{10}O_4$, or $HO(CHOH)_2OH$; specifically, one particular stereoisomer with that formula.

"Stevia" is a natural sweetener and sugar substitute derived from the leaves of the plant species Stevia rebaudiana, native to Brazil and Paraguay. Stevia is probably the healthiest option, followed by xylitol, erythritol, and yacon syrup. Natural sugars like maple syrup, molasses, and honey are less harmful than regular sugar and even have health benefits. Stevia has no calories, and it is 200 times sweeter than sugar in the same concentration.

In an embodiment, sweetener is low-calorie sweetener.

"Low-calorie sweetener" refers to a sweetener with a calorie value less than 3. In an embodiment, calorie value of a low-calorie sweetener is less than 2.5, less than 2.4, less than 2.3, less than 2.2, less than 2.1, less than 2, less than 1.5, less than 1, less than 0.5 or less.

In an embodiment, low-calorie sweetener is a sugar substitute that provides a sweet taste like that of sugar while containing significantly less food energy than sugar-based sweeteners thus making it a zero-calorie (non-nutritive) or low-calorie sweetener.

In an embodiment, artificial sweeteners may be derived through manufacturing of plant extracts or processed by chemical synthesis. Sugar alcohols such as erythritol, xylitol, and sorbitol are derived from sugars. In 2017, sucralose was the most common sugar substitute used in the manufacture of foods and beverages. For example, but not limited to Aspartame, Cyclamate, Steviol glycosides (*Stevia*), Acesulfame potassium (Ace-K) etc. Ace-K is 200 times sweeter than sucrose (common sugar), as sweet as aspartame, about two-thirds as sweet as saccharin, and one-third as sweet as sucralose. Like saccharin, it has a slightly bitter aftertaste, especially at high concentrations.

The term "Alkaline" refers to a part of pH scale. A substance is alkaline if it has a pH over 7.

In an embodiment, alkaline pH ranges from above 7 and up to 14. A pH of 14 is completely alkaline. In an embodiment, a composition according to one or more embodiments of this invention has a pH of about 8 and above, about 9 or above, about 10 or above, about 11 or above, about 12 or above, or about 13 or above.

"Natural oil" and the like refers to oil derived from plant or animal sources. As used herein, these phrases encompass natural oil derivatives as well, unless otherwise indicated. These are triglycerides in which the glycerin is esterified with three fatty acids. They are the main constituent of vegetable oil and animal fats.

In an embodiment, natural oil is also called as natural oil polyols, also known as NOPs or bio polyols, are polyols derived from vegetable oils by several different techniques. The primary use for these materials is in the production of polyurethanes.

There are a limited number of naturally occurring vegetable oils (triglycerides) which contain the unreacted hydroxyl groups that account for both the name and important reactivity of these polyols. Castor oil is the only commercially available natural oil polyol that is produced directly from a plant source: all other NOPs require chemical modification of the oils directly available from plants.

Ninety percent of the fatty acids that make up castor oil is ricinolein acid which has a hydroxyl group on C-12 and a carbon-carbon double bond.

Other vegetable oils—such as soybean oil, peanut oil, and canola oil-contain carbon-carbon double bonds, but no hydroxyl groups. There are several processes used to introduce hydroxyl groups onto the carbon chain of the fatty acids, and most of these involve oxidation of the C—C double bond.

"Natural oil derivatives" refers to compounds and/or mixture of compounds derived from a natural oil using any one or combination of methods known in the art, including but not limited to saponification, transesterification, esterification, amidification, amination, hydrogenation (partial or full), isomerization, oxidation, reduction, and the like, and combinations thereof.

Chain lengths of the fatty acids in naturally occurring triglycerides can be of varying lengths, but 16, 18 and 20 carbons are the most common.

In an embodiment, coconut oil is a natural oil.

In an embodiment, natural oils are selected without limitation from castor oil, coconut oil, corn oil, sesame oil, almond oil, cottonseed oil, olive oil, palm oil, peanut oil, safflower oil, soybean oil, rapeseed oil, mango butter, hemp seed oil, sweet almond oil, jojoba oil, apricot oil, or palm kernel oil, coconut oil, grape seed oil, sunflower oil, avocado oil, tea tree oil, or shea oil, cinnamon bark oil, cocoa oil, coffee oil, cognac oil, ravensara oil, tansy blue oil, vanilla oil or yarrow oil.

In an embodiment, amount of natural oil or its derivatives in the composition is about 0.05% v/w, about 0.1% v/w, about 0.15% v/w, about 0.2% v/w, about 0.25% v/w, about 0.3% v/w, about 0.35% v/w, about 0.4% v/w, about 0.45% v/w, about 0.5% v/w, about 0.75% v/w, about 1% v/w, about 1.25% v/w, about 1.5% v/w, about 1.75% v/w, about 2% v/w, about 2.25% v/w, about 2.5% v/w, about 3% v/w, about 3.5% v/w, about 4% v/w, about 4.5% v/w, about 5% v/w, about 5.5% v/w, about 6% v/w, about 6.5% v/w, about 7% v/w, about 7.5% v/w, about 8% v/w, about 8.5% v/w, about 9% v/w, about 9.5% v/w, about 10% v/w or more.

"Glycerin" is also called glycerol. It is a simple polyol compound. It is a colorless, odorless, viscous liquid that is sweet-tasting and non-toxic. It is also written as glycerin or glycerol or glycerin.

Glycerin is a natural ingredient found in most oral care products to better preserve and sweeten them. A natural agent, glycerin in toothpaste also helps retain the moisture of the paste so it doesn't dry out in the tube.

Glycerin is a colorless, odorless, viscous liquid that is sweet-tasting and non-toxic. The glycerol backbone is found in lipids known as glycerides. Due to having antimicrobial and antiviral properties, it is widely used in FDA approved wound and burn treatments. It is also widely used as a sweetener in the food industry and as a humectant in pharmaceutical formulations. Owing to the presence of three hydroxyl groups, glycerol is miscible with water and is hygroscopic in nature. A mouthwash or gargle historically has been a liquid product used to clean the oral cavity and freshen the breath. The ability to obtain glycerin commercially either as 96% material or 99+% is a feature of glycerin which endows it with a very important capability in oral care product manufacturing.

Water and glycerin are mixed with the particles (including erythritol and rice flour) to form a pickering emulsion. Glycerin can also act as a humectant to prevent water loss, and any number of flavoring agents can be added from natural sources (such as jasmine extract, grapefruit oil, etc.). Glycerin may form a dispersed or discontinuous phase in the pickering emulsion.

Glycerin may be added including but not limited to a concentration of about 3% or more, about 4% or more, about 5% or more, and any ranges between and including the weight percentages provided.

In an exemplary embodiment, the dental care products contain glycerin at the following concentrations: at least about 10%, at least about 15%, at least about 20%, at least about 25%, at least about 30% by weight, at least about 35% by weight, or any concentration between and including the provided percent concentrations of the dental care product.

In an embodiment, teeth whitening composition comprises peroxide compounds. The term "teeth whitening" is also cleaning of teeth. In one embodiment, suitable peroxide compounds comprise hydrogen peroxide and organic peroxides including urea peroxide, glyceryl peroxide, or benzoyl peroxide. A preferred peroxide is hydrogen peroxide.

Typically, the peroxide compound can be employed in the composition of the present invention in amounts so that at least about 1% by weight of the composition comprises a peroxide. Preferably, the peroxide compound comprises from about 2 to about 30% by weight of the composition for example from about 2% to about 5%, from about 5% to about 10%, from about 10% to about 15%, from about 15% to about 20%, from about 20% to about 25% or from about 25% to about 30% by weight of the composition. More preferably, the peroxide comprises from about 3 to about 15% by weight of the composition.

In an embodiment, teeth whitening composition comprises about 6 wt % hydrogen peroxide or less, in particular about 0.1 wt % to about 6 wt % hydrogen peroxide.

In an embodiment, range of hydrogen peroxide in the composition vary from 0.1 wt %, 0.5 wt %, 1 wt %, 1.5 wt %, 2 wt %, 2.5 wt %, 3 wt %, 3.5 wt %, 4 wt %, 4.5 wt %, 5 wt %, 5.5 wt %, or 6 wt %.

In an embodiment, the composition does not contain glycerin.

In an embodiment, toothpaste does not contain glycerin.

In an embodiment, calcium carbonate is a main ingredient to help with binding (instead of glycerin) in a composition.

In an embodiment, the composition contains glycerin less than 5% w/W, 4% w/W, 3% w/W, 2% w/W, 1% w/W, 0.5% w/W or 0.1% w/W of the formulation.

"Fluoride" is an inorganic, monatomic anion of fluorine, with the chemical formula $F^-$, whose salts are typically white or colorless. Fluoride salts typically have distinctive bitter tastes and are odorless. Fluoride can be added to water or toothpaste to help prevent unhealthy teeth. Fluoride is the simplest fluorine anion. In terms of charge and size, the fluoride ion resembles the hydroxide ion.

The fluoride in toothpaste has beneficial effects on the formation of dental enamel and bones. Sodium Fluoride (NaF) is the most common source of fluoride, but Stannous Fluoride ($SnF_2$), and Sodium Monofluorophosphate ($Na_2PO_3F$) are also used.

Fluoride-containing toothpaste can be acutely toxic if swallowed in large amounts, but instances are exceedingly rare and result from prolonged and excessive use of toothpaste (i.e., several tubes per week). Approximately 15 mg/kg body weight is the acute lethal dose, even though an amount as small as 5 mg/kg may be fatal to some children.

The risk of using fluoride is low enough that the use of full-strength toothpaste (1350-1500 ppm fluoride) is advised for all ages. However, smaller volumes are used for young children, for example, a smear of toothpaste until three years old.

In an embodiment, the composition does not contain fluoride.

"Sodium bicarbonate", commonly known as baking soda or bicarbonate of soda, is a chemical compound with the formula $NaHCO_3$. It is a salt composed of sodium cation and Bicarbonate anion. Sodium Bicarbonate is a white solid that is crystalline, but often appears as a fine powder. It is a chemical compound with the formula $NaHCO_3$. It is a salt composed of a sodium cation ($Na^+$) and a bicarbonate anion ($HCO_3^-$). It has a slightly salty, alkaline taste resembling that of washing soda (Sodium Carbonate). The natural mineral form is nahcolite. It is a component of the mineral natron and is found dissolved in many mineral springs. It has weak disinfectant properties, and it may be an effective fungicide against some organisms.

"Flavoring agents" are key food additives with hundreds of varieties like fruit, nut, seafood, spice blends, vegetables and wine which are natural flavoring agents. Besides natural flavors, there are chemical flavors that imitate natural flavors. Some examples of chemical flavoring agents are alcohols that have a bitter and medicinal taste, esters are fruity, ketones and pyrazines provide flavors to caramel, phenolics have a smokey flavor and terpenoids have *citrus* or pine flavor.

In an embodiment, toothpaste flavors are Spearmint, Peppermint, Wintergreen, Cinnamon, Bourbon, Rye, Anise, Clove, Caraway, Coriander, *Eucalyptus*, Nutmeg, Menthol, and Thyme.

In an embodiment, there could be fun flavors, like Vanilla, Strawberry, Bubblegum, and Jasmine etc. Flavors include all commercially available flavors as well as custom formulations.

In an embodiment, flavoring agents could be natural flavoring substances. These flavoring substances are obtained from plant or animal raw materials, by physical, microbiological, or enzymatic processes. They can be used in either their natural state or processed for human consumption but cannot contain any nature-identical or artificial flavoring substances.

In an embodiment, flavoring agents could be nature-identical flavoring substances. These are obtained by synthesis or isolated through chemical processes, which are chemically and organoleptically identical to flavoring substances naturally present in products intended for human consumption.

In an embodiment, artificial flavoring substances could also be used as a flavoring agent. Artificial flavoring substances are not identified in a natural product intended for human consumption. These are typically produced by fractional distillation and chemical manipulation of naturally sourced chemicals, crude oil, or coal tar. Despite their chemical differences, they have the same sensory characteristics as natural ones.

The majority of artificial flavors are specific and often complex mixtures of singular naturally occurring flavor compounds that are combined to either imitate or enhance a natural flavor. These mixtures are formulated by flavorists to give a food product a unique flavor and to maintain flavor consistency between different product batches or after recipe changes. The list of known flavoring agents includes thousands of molecular compounds, and the flavor chemist (flavorist) can often mix these together to produce many common flavors. Many flavorants consist of esters, which are often described as being "sweet" or "fruity".

In an embodiment, flavoring agents are present in an amount from about 0.01% to about 5% by weight of the composition for example, from about 0.01% to about 0.05%, 0.05% to about 1%, 1% to about 1.5%, 1.5% to about 2%, 2% to about 2.5%, 2.5% to about 3%, 3% to about 3.5%, 3.5% to about 4%, 4% to about 4.5% by weight of the composition.

"Surfactant" is a compound that lowers the surface tension between two liquids, between a gas and a liquid, or between a liquid and a solid. Surfactants may act as detergents, wetting agents, emulsifiers, foaming agents, or dispersants. Surfactants have specific physical properties resulting in decreases in the interfacial tension between different phases (i.e., oil and water) and corresponding micelle formation depending on the hydrophile-lipophile properties of the surfactants. Resultant dispersions of oil and water can be monophasic, biphasic or triphasic systems.

"Suspension" is a heterogeneous mixture in which the solute particles do not dissolve, but get suspended throughout the bulk of the solvent, left floating around freely in the medium. The internal phase (solid) is dispersed throughout the external phase (fluid) through mechanical agitation, with the use of certain excipients or suspending agents. "Suspending agents" are hydrophilic colloids, such as but not limited to cellulose derivatives, acacia, and xanthan gum that are added to a suspension to increase viscosity, inhibit agglomeration, and decrease sedimentation.

In an embodiment, a suspending agent includes at least one ethoxylated or ethoxylated-amidated plant oil. The suspending agent may have two different ethoxylated or ethoxylated-amidated plant oils. The suspending agent may have at least three different ethoxylated or ethoxylated-amidated plant oils. The ethoxylated or ethoxylated-amidated plant oil may be, for example, ethoxylated or ethoxylated-amidated plant oil forms of castor oil, coconut oil, corn oil, sesame oil, almond oil, cottonseed oil, olive oil, palm oil, peanut oil, safflower oil, soybean oil, or rapeseed oil.

In some embodiments, the suspending agent includes one or more of ethoxylated coconut oil, ethoxylated castor oil or ethoxylated-amidified coconut oil.

In some embodiments, the suspending agent has at least one ethoxylated or ethoxylated-amidated plant oil, and at least one nonionic alkyl glycoside cross polymer. In some embodiments, the only surfactants in the composition are alkyl glycoside cross polymers.

In an embodiment, the suspending agent could be a surfactant. In some embodiments, the composition comprises from about 0.01% to about 5%, optionally from about 0.05% to about 3%, optionally from about 0.05% to about 1%, or optionally from about 0.05% to about 0.5%, by weight of the composition of a suspending agent.

In an embodiment, the NHAP in a suspension is 10-50 nm in size. In an embodiment, a size range of NHAP particles is selected from a minimum value being either 1 nm, 5 nm, 10 nm, 20 nm or 25 nm and the maximum value being either 20 nm, 25 nm, 30 nm, 35 nm, 40 nm, 45 nm, 50 nm or more.

In an embodiment, NHAP suspension could be produced synthetically by wet chemical precipitation according to WO2005077508. The process is relatively simple and can be described by the following 3 steps: 1. prepare inorganic solutions from calcium and phosphorous salts; 2. feed the solutions to reactor where they precipitate as a NHAP suspension; 3. concentrate this suspension to 15.5±0.5% wt. NHAP to obtain a paste product. The process is carried out in purified water and at room temperature. There are no complex compounds or chemicals. In an embodiment, the starting agents for preparing the NHAP suspension are inorganic calcium, phosphorous, and potassium salts, as well as water.

In an embodiment, NHAP in toothpaste are <50 nanometers (i.e., 0.050 microns), with a nano-rod shape having a width between 5-20 nm (typically close to 10 nm) and length below 50 nm (typically between 30 to 40 nm). These small nano-sized particles are very effective in doing dentine tubule occlusion and enamel remineralization.

"Plant product" signifies a product of plant origin in an unprocessed state or having undergone only simple preparation, such as milling, drying, or pressing, but excluding plants. In an embodiment, plant product comprises a natural oil.

In an embodiment, a plant product can also be prepared by chemical synthesis (both semi synthesis and total synthesis). The term plant product has also been extended for commercial purposes to refer to cosmetics, dietary supplements, and foods produced from natural sources.

"Dental product" herein signifies specially fabricated material, designed for use in dentistry. There are many different types of dental products, and their characteristics vary according to their intended purpose. Dental composition can be used in different forms and are not limited to toothpaste, tooth serum, floss, tooth wipes, gels, powder, tablets, lozenges, chewing gums, mouth strips, balms, dental filling material, desensitizing agents for teeth, whitening agents for teeth, tooth varnish, dental cements, and the like. Dental composition is alternately called an oral composition. In an embodiment, composition is meant for used as a dental product.

"Floss" is a cord of thin filaments used in interdental cleaning to remove food and dental plaque from between teeth in particular, places difficult or impossible to reach with a toothbrush. Its regular use as part of oral cleaning is designed to maintain oral health.

In an embodiment, the floss comprises nanohydroxyapatite (NHAP). In an embodiment, the floss comprises ecofriendly vegan material which further comprises fibers. The fibers include but are not limited to seaweed, cotton floss, bamboo charcoal, polyester, corn, hemp, cotton, or silk.

"Wipes" are small, saturated, gauze-like pads formulated to help prevent tooth decay. These wipes are one way to administer antimicrobial agents to the mouth in order to reduce the amount of harmful oral bacteria, such as Streptococcus mutans.

In an embodiment, the tooth wipes are organic and biodegradable and comprises 100% cotton with 2×2 gauze. Tooth wipes are used for cleaning and wiping baby teeth, adult teeth, or animal teeth after drinking tea, coffee, lemon water, sugary drinks, acidic drinks, or any non-water drinks, eating colored foods like blueberries or foods with sugar (like candies etc).

In an embodiment, tooth wipes contain NHAP, which is effective in reducing sensitivity and remineralizing teeth.

In an embodiment, tooth serum according to this embodiment, has about 10% NHAP. In another embodiment, tooth serum has NHAP about 15% NHAP, 20% NHAP, 25% NHAP, 30% NHAP, 40% NHAP, 50% NHAP or more in the formulation.

The composition can be packaged in a plastic laminate, a metal tube, or a conventional single compartment dispenser in the form of toothpaste or gel. It can be applied to the surface of the teeth by any physical means, such as a toothbrush, fingertip, or through an applicator directly to the sensitive area. Types of solid dosage form include lozenges, chewing gums, tablets, mouth strips, balms, and the like. These can be packaged in conventional consumer-friendly packaging.

In an embodiment, a tooth wipe is comprised of NHAP, coconut oil, and flavor.

In an embodiment, because toothpastes are not available in plastic, the toothpaste/serum is kept in a glass jar, while the wipes are kept in aluminum containers. Bamboo or glass/stainless steel floss will be used. In an embodiment, toothpaste composition with ingredients in 1 oz. comprises Xylitol (9 tsp), Sodium Bicarbonate (2 tsp), NHAP suspension (1.05 tsp, to make 1% NHAP in the paste), Coconut Oil (5 tsp), Peppermint Oil (8 drops), Salt (0.02 tsp).

In an embodiment, toothpaste is alkaline.

The pH of the toothpaste is more than 7, more than 8, more than 9 or more than 10, more than 11 or more.

Alkaline toothpaste does not contain glycerin and surfactants. This toothpaste contains less chemicals and preservatives than the majority of toothpastes in the market.

Toothpaste contains NHAP (1%-65%) in solution with baking soda, coconut oil and peppermint oil. In an embodiment, the NHAP in solution could be about 1%-15%, 1%-20% or 1%-25%, 5%-10% 5%-20%, 5%-25%, 5%-30%, 1%-30% or 1%-40% in solution of toothpaste.

In an embodiment, the toothpaste could have any amount of NHAP and any size of NHAP as described in various embodiments of this invention. In an embodiment, toothpaste has NHAP with particle size less than 50 nm, less than 40 nm, less than 30 nm, less than 20 nm, less than 10 nm or lesser.

The NHAP in suspension is 20-50 nm in size. NHAP in suspension could be about 10 nm-50 nm, 10-30 nm, less than 20 nm, less than 10 nm or 10-50 nm. The size of NHAP in suspension could be any size as described in any embodiments of this invention.

In an embodiment, composition contains dispersed, therein visible, palpable, agglomerated particles of a dental polishing agent that are substantially insoluble in the toothpaste and are easily reduced to impalpable particles of a dental polishing agent during toothbrushing.

In an embodiment, polishing agents thus include insoluble phosphate salts, such as insoluble sodium metaphosphate, insoluble potassium metaphosphate, calcium pyrophosphate, magnesium orthophosphate, trimagnesium orthophosphate, tricalcium phosphate, dicalcium phosphate dihydrate, anhydrous dicalcium phosphate and the like, calcium carbonate, magnesium carbonate, hydrated alumina, silica, zirconium silicate, aluminum silicate including calcined aluminum silicate and polymethyl methacrylate.

(e.g., between 0.1 and 10 microns) are particularly suitable for use in the agglomerates. Representative of such materials are silica, zirconium silicate, aluminum silicate, calcined aluminum silicate, calcium silicate, silicon carbide, pumice, ilmenite ($FeTiO_3$), $CeO_2$, $Fe_2O_3$ (hematite), $SnO_2$, Topaz (aluminum hydroxy fluoro silicate) and $TiO_2$, either natural or manufactured. When incorporated into a toothpaste, agglomerated particles of hard abrasive materials as defined above e.g., MOH hardness greater than 5 and particle size between 0.1 and 10 microns, make it possible to provide substantially increased cleaning and polishing properties to the formulation, without significantly increasing abrasion to the dental hard tissues, (enamel, dentin and cementum).

In an embodiment, a product characterization of NHAP in toothpaste is shown in Table 1.

TABLE 1

Product characterization of NHAP in toothpaste.

| SECTION 1: PRODUCT IDENTIFICATION | |
|---|---|
| Trade name | nanoXIM•CarePaste |
| SKU | 504102 |
| INCI name | Hydroxyapatite (nano) |
| IUPAC name | Pentacalcium hydroxide triphosphate |
| CAS number | 12167-74-7 |
| EC number | 235-330-6 |
| Synonyms | Hydroxyapatite (CAS No. 1306-06-5) |
| Chemical formula | $Ca_{10}(PO_4)_6(OH)_2$ |
| REACH ID number | 01-2119490075-38-0021 |

| SECTION 2: PRODUCT INFORMATION | |
|---|---|
| Lot number | F09-011 |
| Production date | September 2020 |
| Expiry date | September 2023 |
| Particle size | <50 nm |
| Shelf life | 3 years |
| Physical appearance | White aqueous suspension |

SECTION 3: LOT CHARACTERIZATION

| | Unit | Analysis | Results | Specification | Reference method |
|---|---|---|---|---|---|
| Solids | wt % | Lot | 20.3 | 20.0 ± 1.0 | Ph. Eur. 7th Ed.2.2.32. |
| Hydroxyapatite, $Ca_{10}(PO_4)_6(OH)_2$ | wt % | Lot | 15.7 | 15.5 ± 0.5 | IT-07-NET* |
| Potassium Chloride, KCl | wt % | Lot | 4.5 | 4.5 ± 0.5 | IT-07-NET* |
| Water, $H_2O$ | wt % | Lot | 79.7 | 80.0 ± 1.0 | IT-07-NET* |
| pH @ 25° C. | | Lot | 10.2 | 10.0 ± 0.5 | IT-03-NET* |
| Total heavy metals (as Pb) | ppm | Lot | <12 | ≤20 | Ph. Eur. 7th Ed. 2.4.8. |
| Total Aerobic Mesophilic Microorganisms (bacteria, yeast & mold) | cfu/g | Lot | <3 | ≤100 | ISO 11737-1:2006 |

In an embodiment, MOH hardness of at least 5 and particle size such as to be useful as a dental polishing agent In an embodiment, another product characterization of NHAP in toothpaste is shown in Table 2.

TABLE 2

Product characterization of NHAP in toothpaste

| SECTION 1: PRODUCT IDENTIFICATION | |
|---|---|
| Trade name | nanoXIM•CarePaste |
| SKU | 504102 |
| INCI name | Hydroxyapatite (nano) |
| IUPAC name | Pentacalcium hydroxide triphosphate |

TABLE 2-continued

Product characterization of NHAP in toothpaste

| CAS number | 12167-74-7 |
|---|---|
| EC number | 235-330-6 |
| Synonyms | Hydroxyapatite (CAS No. 1306-06-5) |
| Chemical formula | $Ca_{10}(PO_4)_6(OH)_2$ |
| REACH ID number | 01-2119490075-38-0021 |

SECTION 2: PRODUCT INFORMATION

| Lot number | F11-015 |
|---|---|
| Production date | November 2020 |
| Expiry date | November 2023 |
| Particle size | <50 nm |
| Shelf life | 3 years |
| Physical appearance | White aqueous suspension |

SECTION 3: LOT CHARACTERIZATION

| | Unit | Analysis | Results | Specification | Reference method |
|---|---|---|---|---|---|
| Solids | wt % | Lot | 19.9 | 20.0 ± 1.0 | Ph. Eur. 7th Ed.2.2.32. |
| Hydroxyapatite, $Ca_{10}(PO_4)_6(OH)_2$ | wt % | Lot | 15.4 | 15.5 ± 0.5 | IT-07-NET* |
| Potassium Chloride, KCl | wt % | Lot | 4.5 | 4.5 ± 0.5 | IT-07-NET* |
| Water, $H_2O$ | wt % | Lot | 80.1 | 80.0 ± 1.0 | IT-07-NET* |
| pH @ 25° C. | ppm | Lot | 10.3 | 10.0 ± 0.5 | IT-03-NET* |
| Total heavy metals (as Pb) | | Lot | <12 | ≤20 | Ph. Eur. 7th Ed. 2.4.8. |
| Total Aerobic Mesophilic Microorganisms (bacteria, yeast & mold) | cfu/g | Lot | <4 | ≤100 | ISO 11737-1:2006 |

In an embodiment, tablets are 100% vegan, palm oil free, fluoride free and gluten free.

In an embodiment, ingredients for tablets or paste are Finnish birch xylitol, ozonated aqua, organic coconut glycerin, organic coconut oil, organic cocoa butter, calcium glycerophosphate, sodium bicarbonate, betaine, menthol, organic *Mentha piperita* oil, potassium citrate, sodium anisate, zinc citrate, nanohydroxyapatite, xanthan gum, vegan vitamin K2 in MCT oil, vegan vitamin D3 in MCT oil, organic NZ manuka oil, organic NZ Totarol™. seasonal: erythritol, calcium carbonate, xylitol, natural coconut flavor, hydroxyapatite (nano), natural mango flavor, sodium bicarbonate, natural key lime flavor, guar gum, sodium cocoyl glutamate, zinc citrate, silicon dioxide, cellulose blend.

In an embodiment, ingredients for paste are silica, sorbitol, glycerin, xylitol, hydroxyapatite, calcium carbonate, propanediol, *Potassium cocoate*, *Stevia rebaudiana* extract, *Mentha arvensis* (wild mint) oil, *Mentha piperita* (peppermint) oil, *Cinnamomum cassia* (cinnamon) bark extract, *citrus Aurantium dulcis* (orange) peel oil, *Citrus limon* (lemon) peel oil, *melaleuca* alternifolia (tea tree) oil, cellulose gum, sodium gluconate, menthol, *Thymus vulgaris* (thyme) extract, erythritol, xanthan gum, *Eucalyptus globulus* extract, *Illicium verum* (anise) extract.

In an embodiment, ingredients for paste are aqua, hydrated silica, sorbitol, glycerin, xylitol, potassium nitrate, nanohydroxyapatite, magnesium aluminum silicate, *Mentha piperita* oil, sodium lauroyl sarcosinate, xanthan gum, phenoxyethanol, potassium chloride, sodium sulfate, sodium saccharin, ci 77891.

In an embodiment, ingredients for paste are water, vegetable glycerin, hydrated silica, sorbitol powder, silica, hydroxyapatite (nano), sodium benzoate, sodium lauroyl sarcosinate, *Mentha piperita* essential (peppermint) oil, *Mentha viridis* (spearmint) oil, *Illicium verum* (star anise) oil, *Gaultheria procumberis* (wintergreen) oil, xylitol, xanthan gum, *Stevia rebaudiana* extract powder, methylsulfonylmethane, *Aloe barbadensis* (*Aloe vera*) leaf juice, sodium bicarbonate, *Camellia sinensis* (green tea) leaf extract, *Cucumis sativus* (cucumber) fruit extract, *Persea gratissima* (avocado) fruit extract, *Mangifera indica* (mango) fruit extract, menthol, *Elettaria cardamomum* minuscula seed (cardamom), potassium chloride.

In an embodiment, ingredients for healthy gums toothpaste are *Aloe barbadensis* (*Aloe vera*) leaf juice, vegetable glycerin (soy free), xylitol, hydrated silica (mineral), hydroxyapatite (mineral), calcium carbonate (mineral), and organic *Cocos*.

In an embodiment, ingredients for healthy smile toothpaste are *Aloe barbadensis* (inner leaf) juice, hydroxyapatite (mineral), organic hemp seed oil, organic *Cocos nucifera* (coconut) oil, vegetable glycerin (soy free), calcium ascorbate (vitamin c), *Cinnamomum zeylanicum* (cinnamon) oil, *Eugenia caryophyllus* (clove) oil, *Ocimum sanctum* (tulsi) leaf extract, *Elettaria cardamomum* (cardamom) oil, *Azadirachta indica* (neem) extract, *Potassium cocoate* (from organic coconut), xanthan gum (thickener), *Stevia rebaudiana* leaf/stem extract *officinalis* (rosemary) oil, sodium cocoyl isethionate (from coconuts), *Zingiber officinale* (ginger) root extract.

In an embodiment, ingredients for kids' anti-plaque toothpaste are *Aloe barbadensis* (inner leaf) juice, vegetable glycerin, hydroxyapatite (mineral), calcium carbonate (mineral), hydrated silica (mineral), *Cocos nucifera* (coconut) oil, *maranta*.

In an embodiment, ingredients for kids' mineral toothpaste are *Aloe barbadensis* (inner fillet) leaf juice, vegetable glycerin (soy free), xylitol, hydrated silica (mineral), hydroxyapatite (mineral), calcium carbonate (mineral), *Cocos nucifera*.

In an embodiment, ingredients for anti-plaque toothpaste are mint: *Aloe barbadensis* (*Aloe vera*) leaf juice, vegetable glycerin (soy free), hydroxyapatite (mineral), hydrated silica (mineral), xylitol, calcium carbonate (mineral), organic *Cocos nucifera* (coconut oil), *Mentha piperita* (peppermint oil), *Mentha spicata* (spearmint leaf oil), *Mentha arvensis* (menthol crystals), *Potassium cocoate* (from coconut oil), sodium cocoyl isothionate (from coconut oil), calcium ascorbate (vitamin c), *Azadirachta indica* (neem extract), *Vaccinium macrocarpon* (cranberry fruit extract), *Rosmarinus officinalis* (rosemary leaf extract), xanthan gum (thickener), *Stevia rebaudiana* leaf/stem extract, *Cinnamomum cassia* (cinnamon bark extract), *Illicium verum* (anise extract).

In an embodiment, ingredients for extreme whitening toothpaste—mint: *Aloe barbadensis* (*Aloe vera*) leaf juice, vegetable glycerin (soy free), hydroxyapatite (mineral), hydrated silica (mineral), xylitol, calcium carbonate (mineral), organic *Cocos nucifera* (coconut oil), *Mentha piperita* (peppermint oil), *Mentha spicata* (spearmint leaf oil), *Mentha arvensis* (menthol crystals), *Potassium cocoate* (from coconut oil), sodium cocoyl isothionate (from coconut oil), calcium ascorbate (vitamin c), *Melaleuca alternifolia* (tea tree leaf oil), xanthan gum (thickener), *Stevia rebaudiana* leaf/stem extract, *citrus Aurantium dulcis* (orange peel oil), *Citrus limon* (lemon peel oil), *Azadirachta indica* (neem extract), activated (coconut charcoal), *Illicium verum* (anise extract), sodium chlorite.

In an embodiment, ingredients for healthy gums toothpaste—mint: *Aloe barbadensis* (*Aloe vera*) leaf juice, vegetable glycerin (soy free), hydroxyapatite (mineral), hydrated silica (mineral), xylitol, calcium carbonate (mineral), organic *Cocos nucifera* (coconut oil), *Mentha piperita* (peppermint oil), *Mentha spicata* (spearmint leaf oil), *Mentha arvensis* (menthol crystals), *Potassium cocoate* (from coconut oil), sodium cocoyl isothionate (from coconut oil), calcium ascorbate (vitamin c), *Camellia sinensis* (green tea leaf extract), xanthan gum (thickener), *Azadirachta indica* (neem extract), *Stevia rebaudiana* leaf/stem extract, *Thymus vulgaris* (thyme leaf oil), *Cinnamomum cassia* (cinnamon bark extract), *Illicium verum* (anise extract).

In an embodiment, ingredients for sensitivity relief toothpaste—mint: *Aloe barbadensis* (*Aloe vera*) leaf juice, vegetable glycerin (soy free), hydroxyapatite (mineral), hydrated silica (mineral), xylitol, calcium carbonate (mineral), organic *Cocos nucifera* (coconut oil), organic hemp seed oil, *Mentha piperita* (peppermint oil), *Mentha spicata* (spearmint leaf oil), *Mentha arvensis* (menthol crystals), *Potassium cocoate* (from coconut oil), sodium cocoyl isethionate (from coconut oil), calcium ascorbate (vitamin c), *Chamomilla recutita matricaria* (chamomile flower extract), xanthan gum (thickener), *Stevia rebaudiana* Ned/stem extract, *Cinnamomum cassia* (cinnamon bark extract), *Azadirachta indica* (neem extract), *Salvia officinalis* (sage extract), *Melaleuca alternifolia* (tea tree leaf oil), *Illicium verum* (anise extract).

In an embodiment, a composition of wipes comprises water, glycerin, xylitol, cetylpyridinium chloride, sodium levulinate, octanediol, ethylhexyl glycerin, grapefruit seed extract, *Artemisia princeps* extract.

In an embodiment, a composition of wipes comprises water, xylitol, fruit extract, poly aminopropyl biguanide, citric acid, sodium benzoate.

In an embodiment, a composition of wipes comprises water, *Aloe barbadensis* leaf juice, glycerin, hydrated silica, xylitol, sodium levulinate, sodium phytate, xanthan gum, potassium sorbate. sodium levulinate: a corn derived preservative that is 100% natural and eco-friendly. sodium phytate: a rice bran derivative that is a stabilizer. it is 100% natural and eco-friendly.

In an embodiment, a composition of wipes comprises purified water, xylitol, glycerin, hydroxyethyl cellulose, sodium benzoate, citric acid, sodium citrate and natural grape flavor.

In an embodiment, a composition of wipes comprises peppermint oil, menthol, methyl paraben, propyl paraben, PEG-400, sodium saccharine, starch.

In an embodiment, a composition of wipes comprises peppermint oil, menthol, stevioside.

In an embodiment, a composition of wipes comprises water/aqua/eau, alcohol denat, polysorbate 20, glycerin, sodium bicarbonate, flavor (aroma), *Stevia rebaudiana* extract, *Vaccinium macrocarpon* (cranberry) fruit extract.

In an embodiment, a composition of wipes comprises water, sorbitol, glycerin, hydrogen peroxide, polysorbate 80, *citrus Aurantium dulcis* (orange) juice, calcium carbonate, citric acid, sodium bicarbonate, sodium chloride, disodium EDTA, sodium benzoate.

In an embodiment, a composition of wipes comprises deionized water, potassium sorbate, carbopol, trolamine, organic vegetable glycerin, organic xanthan gum, oleth 20, organic coconut oil (*Cocos nucifera*), organic lemon myrtle (*Backhousia citriodora*), organic.

In an embodiment, a composition could comprise one or more of xylitol, sodium bicarbonate, NHAP, coconut oil, peppermint oil, kava, glycerin, sodium lauryl sulfate, sodium sulfate, sodium lauroyl sarcosinate, sodium cocoyl glutamate, *Potassium cocoate*, silica, sodium benzoate, calcium carbonate, propanediol, potassium nitrate, potassium chloride, xanthan gum, sorbitol, erythritol, *Stevia*, aloe leaf juice, neem extract—*Azadirachta indica*, zinc citrate, silicon dioxide, guar gum, menthol, ozonated aqua, cocoa butter, calcium glycerophosphate, betaine, sodium anisate, K12 in MCT oil, D3 in MCT oil, manuka oil, Totarol™, diatomaceous earth, sodium chlorite.

In an embodiment, a composition could comprise one or more of bamboo, cotton biodegradable, xylitol, coconut oil, NHAP, $NaHCO_3$, peppermint oil, water, glycerin, cetylpyridinium chloride, sodium levulinate, octanediol, ethylhexyl glycerin, grapefruit seed extract, *Artemisia princeps* extract, fruit extract, poly aminopropyl biguanide, citric acid, sodium benzoate, *Aloe barbadensis* leaf juice, hydrated silica, sodium phytate, xanthan gum, potassium sorbate, hydroxyethyl cellulose, sodium citrate, natural flavor, alcohol denat, polysorbate 20, flavor (aroma), fruit extract, *Stevia*, menthol, stevioside, carbopol, trolamine, oleth 20, coconut charcoal, lemon myrtle organic, sorbitol, $H_2O_2$, calcium carbonate and phosphoric acid.

In an embodiment, nanohydroxyapatite (NHAP) can be used in powder form with the particle size ranges from 30-50 micron. In an embodiment, a size range of NHAP particles as a powder form is selected from a value being either 30 micron, 35 micron, 40 micron, 45 micron, or 50 microns. The NHAP in powder or tablet version is most likely 30-50 microns in size (3,000-5,000 nm). In an embodiment, size of NHAP in powder or table is less than 30 micron, 20 micron, 15 micron, 10 micron, 0.1 micron, 0.08 micron, 0.07 micron, 0.06 micron or lesser.

In an embodiment, another product characterization of NHAP in tooth powder is shown in Table 3.

TABLE 3

Characterization of NHAP in powder

SECTION 1: PRODUCT IDENTIFICATION

| | |
|---|---|
| Trade name | nanoXIM•CarePaste |
| SKU | 504202 |
| IUPAC name | Pentacalcium hydroxide triphosphate |
| CAS number | 12167-74-7 |
| EC number | 235-330-6 |
| Synonyms | Hydroxyapatite (CAS No. 1306-06-5) |
| Chemical formula | $Ca_{10}(PO_4)_6(OH)_2$ |
| REACH ID number | 01-2119490075-38-0021 |

SECTION 2: PRODUCT INFORMATION

| | |
|---|---|
| Lot number | I466C5SD |
| Particle size | Microparticles |
| Physical appearance | Spray dryer white and odourless powder |

SECTION 3: LOT CHARACTERIZATION

| | Unit Analysis | Results | Specification | Reference method |
|---|---|---|---|---|
| Assay (calculated on dry basis) | wt % Lot | 95.9 | ≥90 | Ph. Forum 31(2): 2005 |
| Loss on drying | wt % Lot | 2.8 | ≤5 | Ph. Eur. 7th Ed.2.2.32. |
| Salts ($K^+$; $Cl^-$; $Ca^{2+}$) | wt % Lot | 0.2 | ≤3 | Ph. Eur. 7th Ed.2.2.32. |
| Particle size ≤ 100 μm | % Lot | 99.9 | ≥95 | Laser Diffraction |
| Total heavy metals (as Pb) | ppm Lot | <12 | ≤20 | Ph. Eur. 7th Ed. 2.4.8. |

FIG. 1 shows a particle size distribution of NHAP powder.

In an embodiment, dental product further comprises fennel, licorice, CBD, kava (*Piper methysticum*), Lavender, Cacao, Camphor, Lalang oil, Pippali, Garlic, Tomar Beej, Sunthi, Babul Extract, Meswak Extract, calcium carbonate, magnesium, Hawaiian Fine Sea Salt, mustard seed Powder, noni, Essential Oils, bee propolis organic, Clove Cinnamon, Sodium Bentonite, Salt, Moringa, Activated Charcoal, Bentonite Clay, Cinnamon Oil, Clove Oil, Clove Powder, Matcha Powder, Kaolin Clay, Diomatceaus Earth, Neem, Ozone, Peelu, Turmeric, Wheat Grass, Peroxide, Sage, *Stevia*, Thieves Oil, Trace Mineral.

The pH of composition with citric acid and baking soda is shown in FIG. 4. The pH is measured using pH paper, which shows yellow and bluish color in the case of citric acid and baking soda, respectively, indicating their acidic and basic pH.

Three conditions are depicted in FIG. 5: i) Adding solely Citric Acid (CA) to the mixture results in an acidic pH, ii) adding 50 percent Baking Soda (BS) or 50 percent Baking Soda plus a drop of Citric Acid (CA) in a combination resulting in alkaline pH, iii) Adding 50 percent Citric Acid (CA) and 50 percent Baking Soda (BS) results in acidic pH.

In an embodiment, floss comprises NHAP.

In an embodiment, floss is made of ecofriendly vegan material which comprises fibers. Possible fibers which are not limited to Seaweed (Algae) & Cotton Floss, Bamboo Charcoal/Polyester, Corn, Hemp, Cotton, Silk or like.

In an embodiment, tooth wipes are organic 100% cotton biodegradable 2×2 gauze.

Most wipes on the market are water based, not oil based, as a result, more preventatives are required leading to exposure to harmful chemicals to the body.

In an embodiment, tooth wipes are oil based.

"Preservatives" signify a substance or a chemical that is added to products to prevent decomposition by microbial growth or by undesirable chemical changes. In an embodiment, preservatives such as but not limited to Chlorhexidine, Triclosan, Quaternary Ammonium Compounds (such as Benzalkonium Chloride) or Parabens (such as Methyl or Propyl Paraben) may be used in the compositions.

The amount of preservative is typically in the range from 0 to about 1% wt. (w/v) such as 0.1-0.75%, such as 0.3 or 0.6% (w/v), such as 0.6 or 1% (w/v), approximately 0.3 to 0.5%.

In an embodiment, composition is free of preservatives.

"Shelf life" is the recommended maximum time for which products can be stored, during which the defined quality of a specified proportion of the goods remains acceptable under expected (or specified) conditions of distribution, storage, and display. It means shelf life is the length of time that a commodity may be stored without becoming unfit for use, consumption, or sale.

In an embodiment, the composition has a shelf life of more than 3 years. In another embodiment, shelf life of the composition is more than 4 years, 5 years, 6 years, 7 years, 8 years, 9 years, 10 years or more.

In an embodiment, growth of microorganisms in the composition is controlled using pH and KCl.

Tooth wipes comprise coconut oil, nanohydroxyapatite, erythritol, peppermint oil and other flavoring agents.

In an embodiment, tooth wipes comprise *Aloe vera*.

In an embodiment, adding a solution of 90% w/w Coconut Oil and 10% w/w NHAP solution to the wipe. In another embodiment, a solution has Oil (Natural Oil) about 85%, 80%, 75%, 70%, 65%, 60%, 55% or 50%, whereas NHAP is about 10%, 15%, 20%, 25%, 30%, 25%, 40%, 45% or 50% of a wipe. In another embodiment, *Aloe Vera* can be added in composition of tooth wipe.

In an embodiment, tooth wipes have erythritol (safe for animals) and drops of peppermint oil for taste.

In an embodiment, tooth wipe comprises NHAP.

In an embodiment, tooth wipe has aqua, glycerin, xylitol, flavor, sodium benzoate, potassium sorbate, coconut oil, sodium bicarbonate, citric acid, NHAP and more.

In an embodiment, tooth wipes can be used in combination with tooth floss.

In an embodiment, tooth wipes and floss comprise NHAP.

Table 4 shows a composition of tooth wipes according to one embodiment of this invention.

TABLE 4

Ingredients of tooth wipes.

| Ingredients | RANGE % |
| --- | --- |
| AQUA | q.b.->100 |
| GLYCERIN | 1.0-3.0 |
| XYLITOL | 0.1-1.0 |
| FLAVORING AGENT | 0.1-1.0 |
| SODIUM BENZOATE | 0.1-0.5 |
| POTASSIUM SORBATE | 0.1-0.5 |
| COCOS NUCIFERA OIL | <0.1 |
| SODIUM BICARBONATE | <0.1 |
| CITRIC ACID | <0.1 |
| NHAP | <10% |

In an embodiment, tooth serum comprised nanohydroxyapatite to remineralize teeth and reduce sensitivity.

In an embodiment, tooth serum comprised *Aloe vera* as carrier.

In an embodiment, tooth serum comprised of 10% nanohydroxyapatite. In an embodiment, tooth serum has about 10%, 15%%, 20%, 25%, 30%, 35%, 40%, 50% or more NHAP in the composition.

In an embodiment, the composition comprises erythritol instead of xylitol; thus the toothpaste, serum and wipe are all pet friendly.

In an embodiment, tooth ribbon floss (wider floss), teeth whitening product, temporary tooth filling product, dental products with NHAP to be used in dental offices by dentists (pumice for cleaning teeth, serum to reduce sensitivity with high percentage NHAP, teeth whitening with NHAP), sterilizable and reusable floss holder.

In an embodiment, NHAP is natural or synthetic. Natural NHAP could be from a plant source or an animal source. In an embodiment, NHAP is obtained from a plant source. In an embodiment, NHAP is synthetic. In an embodiment, NHAP is vegan.

In an embodiment, dental product comprises natural and organic ingredients. Dental product does not contain glycerin, fluoride, and surfactants.

In an embodiment, dental product comprises NHAP in suspension form and not in powder form.

In an embodiment, dental product comprises NHAP in powder form.

In one embodiment, other ingredients that may be used in the formulations of the dental composition include those conventionally used in toothpaste such as toothpaste bases, abrasives, carriers, flavorings, colorings, stabilizers, preservatives, viscosity enhancers, pH adjusters, sparkles, gelling agents, effervescent agents, thickeners, humectants, desensitizing agents, sensitivity agents, whitening agents, mucosal adhesives, bad breath agents, gingivitis agents, astringents, oxidizing agents, and the like. These may be used in the manner and quantity generally known in the art.

In some embodiments, the powder formulation is in the form of an effervescent powder or an effervescent tablet. In some embodiments, the powder formulation further comprises a remineralization agent. In one embodiment, the remineralization agent is a nanomaterial comprising hydroxyapatite crystals on nanoparticles. In some embodiments, the powder formulation further comprises additional ingredients. At least some of the additional ingredients may comprise flavoring agents.

In an embodiment, the powder formulation is in the form of a tablet or a beadlet. A beadlet is defined as a spherical, free-flowing granule with a narrow size distribution. In an embodiment, a beadlet is like a gel capsule with the toothpaste inside and it dissolves in the mouth. In an embodiment, a beadlet has a size of about 500 μm, about 1000 μm, about 2000 μm, about 4000 μm, about 6000 μm, about 8000 μm, about 10 mm, about 20 mm, about 30 mm, about 40 mm, about 50 mm, about 60 mm, about 70 mm, about 80 mm, about 90 mm, about 1 cm, about 1.5, about 2 cm or more.

Antibacterial agents such as triclosan, zinc chloride, and zinc citrate may be used also in conventional amounts and often less than 5% wt./wt. (0.1 to 5%) and indeed less than 1% wt./wt. Where xylitol is used as a sweetener, if more than 2% is used, it can also act as an antimicrobial agent. Preservatives such as Phenoxyethanol may also be used in conventional amounts, usually less than 2% wt./wt. (0.1 to 2%) and indeed often less than 1%.

In an embodiment, toothpaste comprises erythritol 24 g, calcium carbonate 16 g, sodium bicarbonate 4 g, NHAP suspension, 10 g, coconut oil 4 g, peppermint oil 2 g. The NHAP is taken from a stock suspension containing NHAP in 16.66% w/v.

In some embodiments, the acid in the dental composition is selected from citric acid, tartaric acid, fumaric acid and malic acid, and combinations thereof. In one embodiment, the acid in the dental composition is citric acid.

In an embodiment, powder is comprised of ingredients in a specific order. Starting with xylitol and sodium bicarbonate (baking soda), then add the nanohydroxyapatite suspension, then slowly add the coconut oil while mixing everything together and then add the peppermint oil at the end.

The compositions of the embodiments herein are biocompatible, antibacterial, sterilizable, nontoxic, non-mutagenic, non-carcinogenic, radiopaque, impervious to moisture, and do not provoke any adverse immune response.

In an embodiment, whitening agents comprise but are not limited to alumina, phosphates such as sodium hexametaphosphate, charcoal, and polyvinylpyrrolidone (PVP).

In an embodiment, the composition comprises tooth whitening compositions, hydrogen peroxide (and its adducts or association complexes, such as carbamide peroxide and sodium percarbonate). the peroxide source is hydrogen peroxide, or a hydrogen peroxide precursor and the source of acetyl or functionally similar groups are C1-C5 molecule having between 1 to 5 labile C1-C5 acyl containing groups. Alternatively, in order to prevent premature reaction of the hydrogen peroxide or its precursor with the source of acetyl groups, an anhydrous formulation containing both the source of acetyl groups and hydrogen peroxide, or its precursor is provided. The hydrogen peroxide or its precursor, and the source of acetyl groups, upon placement against the stained tooth surface in the oral cavity, are activated by the aqueous content of the saliva to generate a peroxyacid, such as peroxyacetic acid.

Alternatively, a composition may be manufactured having each of the hydrogen peroxide or its precursor and the source of acetyl groups as a separate and distinct component.

The hydrogen peroxide precursor for use in connection with the present invention is preferably selected from the group consisting of carbamide peroxide, sodium percarbonate, sodium perborate, calcium peroxide, magnesium peroxide, sodium peroxide, and the anhydrous poly(vinyl pyrrolidone)/hydrogen peroxide complexes. It is contemplated that any compound which, when in contact with water, is capable of generating, converting to, or otherwise becoming hydrogen peroxide or peroxide anion, will have utility in the formulation of the present inventive compositions. For instance, it is possible to utilize other alkali metal percarbonates (such as potassium percarbonate), as well as enzymatic sources of hydrogen peroxide, such as glucose oxidase in combination with beta-D-glucose. Additional useful peroxide precursors will become apparent to those skilled in the art based upon the present disclosure.

The peroxide precursor is present in the compositions of the present invention as they are applied directly to the tooth surface in an amount sufficient to result in a hydrogen peroxide concentration of from about 0.1 percent by weight to about 15 percent by weight. Higher levels of hydrogen peroxide may be used in conjunction with a supervised dental whitening procedure in which the soft tissue (i.e., the gingival and other mucosal surfaces) are physically isolated from the teeth being whitened. Hydrogen peroxide concentrations up to about 3 percent are acceptable for short-term (less than 60 minutes) incidental contact with soft tissue.

Unexpectedly, the stable oral care compositions of the present invention result in the remineralization of teeth (that is, the formation of new hydroxyapatite) and the whitening of teeth (which can be immediate and predicted through the calcium salt nucleus of the source). As a result of the oral care composition coming into contact with the enamel and/or dentin of the teeth. Furthermore, after using the compositions of the present invention, the teeth are preferably less sensitive, and/or brighter, the same also being a direct result of the formation of hydroxyapatite in situ. The result was tested on primary and permanent dentition.

In an embodiment, any of the formulations/composition disclosed in this specification may also be used for cosmetic products and leave-on and rinse-off cosmetic products for hair, skin, lips, face and nails.

In an embodiment, any of the formulations/composition disclosed in this specification may also be used for polishing and buffing of other surfaces such as household fixtures, appliances and automobiles.

Working Examples

Use of Tooth Wipes on Primary Teeth

Tooth wipes can be used to clean the teeth of a baby or child. These wipes were tested for six months on 3-year-old's baby's teeth, and the result showed that wipes eliminated all plaque visible to the naked eye from the teeth. Result of tooth wipes is shown in FIG. 16.

Use of Tooth Wipes on Permanent Teeth

Tooth wipes were tested for six months on adult teeth to ensure that it could remove all the stained plaque, which it did. Tooth wipes were also tested on adult teeth for six months to determine if it could remove spoilage, and the results were positive. Tooth wipes can also help to reduce teeth sensitivity.

Use of Toothpaste Tested on Permanent Dentition.

Toothpaste was tested for six months on adult teeth to ensure that it could remove all the stained plaque, which it did. Toothpaste was also tested on adult teeth for six months to determine if it could remove spoilage, and the results were positive. Toothpaste can also help to reduce teeth sensitivity. FIG. 3 shows results of use of toothpaste according to this embodiment.

Use of Tooth Paste on Primary Teeth

Toothpaste can be used to clean the teeth of a baby or child. These pastes were tested for six months on 3-year-old's baby's teeth, and results showed that toothpaste eliminated all plaque visible to the naked eye from the teeth.

Use of Tooth Floss on Primary Teeth

Tooth floss can be used to clean the teeth of a baby or child. The floss was tested for six months on a 3-year-old baby's teeth, and the result showed that floss eliminated all plaque visible to the naked eye from the teeth.

Use of Tooth Floss on Permanent Teeth

Tooth floss was tested for six months on adult teeth to ensure that it could remove all the stained plaque, which it did. Tooth floss was also tested on adult teeth for six months to determine if it could remove spoilage, and the results were positive. Tooth floss can also help to reduce teeth sensitivity.

REFERENCES

All references, including granted patents and patent application publications, referred herein are incorporated herein by reference in their entirety.

US20210069096A1—Enhanced Toothpaste and Kits
US20150238399A1—Tooth whitening composition
U.S. Pat. No. 1,045,633B2—Oral hygiene compositions and methods
US20090263497A1—Production method for calcium phosphate nano-particles with high purity and their use
U.S. Pat. No. 9,180,318B2—Stable oral care compositions
U.S. Pat. No. 5,833,959A—Composition for dental issue
US20040101493A1—Chewable solid unit dosage forms and methods for delivery of active agents into occlusal surfaces of teeth
U.S. Pat. No. 4,374,822A—Oral composition
U.S. Pat. No. 5,302,375A—Oral composition having improved tooth whitening effect
U.S. Pat. No. 5,496,541A—Tasteful toothpaste and other dental products
U.S. Pat. No. 5,670,138A—Mouth-care products
U.S. Pat. No. 6,177,097B1—Solid oral anticariogenic composition for cleaning the oral cavity and the teeth, and a process for producing same
US20030198606A1—Patches for teeth whitening
U.S. Pat. No. 6,221,341B1—Tooth whitening compositions
U.S. Pat. No. 8,434,933B2—Network mixer and related mixing process
U.S. Pat. No. 3,935,306A—Toothpaste formulations
U.S. Pat. No. 9,161,895B1—Compositions and methods for improving overall tooth health and appearance
U.S. Pat. No. 6,221,341B1—Tooth whitening compositions
US20150238399A1—Tooth whitening composition
US20050019276A1—Tooth whitening hydrogels

What is claimed is:

1. A dental product comprising a composition, wherein 1 oz. of the composition comprises:
   about 9 tsp of a sweetener selected from xylitol, erythritol and/or *Stevia*,
   about 2 tsp of sodium bicarbonate,
   about 1.05 tsp of a nanohydroxyapatite (NHAP) suspension stock having the NHAP in a range of 16.66% w/v and having a particle size in a range of about 10 nm to 50 nm, and peppermint oil and coconut oil,
   wherein the composition does not contain glycerin, surfactant, preservative and fluoride,
   wherein the composition is alkaline.

2. The product of claim 1, wherein the composition further comprises a flavoring agent.

3. The product of claim 1, wherein the composition further comprises a peroxide compound.

4. The product of claim 3, wherein the peroxide compound comprises hydrogen peroxide and organic peroxide.

5. The product of claim 1, wherein the dental product comprises a toothpaste having a shelf life of about 3 years.

6. The product of claim 1, wherein 1 oz. of the composition contains less than 12 ppm of lead.

7. The product of claim 1, wherein the composition further comprises KCl.

8. A dental product, wherein 1 oz. of the product consists of:
- about 9 tsp of a sweetener selected from xylitol, erythritol and/or *Stevia;*
- about 2 tsp of sodium bicarbonate;
- about 1.05 tsp of a nanohydroxyapatite (NHAP) suspension stock having the NHAP in a range of 16.66% w/v and having a particle size in a range of about 10 nm to 50 nm;
- peppermint oil; and
- coconut oil, wherein the composition is alkaline.

* * * * *